United States Patent
Fan et al.

(12)

(10) Patent No.: US 10,471,060 B2
(45) Date of Patent: Nov. 12, 2019

(54) AMINO PYRIMIDINE COMPOUNDS USEFUL AS SSAO INHIBITORS

(71) Applicant: Eli Lilly and Company, Indianapolis, IN (US)

(72) Inventors: Mengyang Fan, Indianapolis, IN (US); Luoheng Qin, Indianapolis, IN (US); Yi Wei, Indianapolis, IN (US); Guoqiang Zhou, Indianapolis, IN (US); Jingye Zhou, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/356,895

(22) Filed: Mar. 18, 2019

(65) Prior Publication Data

US 2019/0275041 A1    Sep. 12, 2019

Related U.S. Application Data

(63) Continuation of application No. 16/012,140, filed on Jun. 19, 2018, now Pat. No. 10,278,970, which is a continuation of application No. PCT/US2018/017152, filed on Feb. 7, 2018.

(30) Foreign Application Priority Data

Feb. 14, 2017   (WO) ................ PCT/CN2017/000157
Dec. 21, 2017   (WO) ................ PCT/CN2017/117791

(51) Int. Cl.
   *C07D 471/10*     (2006.01)
   *A61K 31/506*     (2006.01)
   *A61P 1/16*       (2006.01)

(52) U.S. Cl.
   CPC .............. *A61K 31/506* (2013.01); *A61P 1/16* (2018.01); *C07D 471/10* (2013.01)

(58) Field of Classification Search
   None
   See application file for complete search history.

(56) References Cited

U.S. PATENT DOCUMENTS

| | | | |
|---|---|---|---|
| 8,716,470 B2 | 5/2014 | Yoshihara et al. | |
| 9,302,986 B2 | 4/2016 | Deodhar et al. | |
| 10,278,970 B2 | 5/2019 | Mengyang et al. | |
| 10,287,270 B2 | 5/2019 | Coates et al. | |
| 2014/0315882 A1 | 10/2014 | Fleck et al. | |
| 2014/0343083 A1 | 11/2014 | Heine et al. | |
| 2018/0296560 A1 | 10/2018 | Fan et al. | |
| 2018/0297987 A1 | 10/2018 | Coates et al. | |

FOREIGN PATENT DOCUMENTS

| | | |
|---|---|---|
| CN | 103459369 A | 12/2013 |
| CN | 104520268 A | 4/2015 |
| JP | 2011136942 A | 7/2011 |
| WO | WO-2008/123469 A1 | 10/2008 |
| WO | WO-2009/012573 A1 | 1/2009 |
| WO | WO-2009/066152 A2 | 5/2009 |
| WO | WO-2014/078609 A1 | 5/2014 |
| WO | WO-2016/042332 A1 | 3/2016 |
| WO | WO-2018/027892 A1 | 2/2018 |
| WO | WO-2018/028517 A1 | 2/2018 |
| WO | WO-2018/148856 A1 | 8/2018 |
| WO | WO-2018/149226 A1 | 8/2018 |

OTHER PUBLICATIONS

Jarolimek, W. et al. (Dec. 31, 2015). "Phase 1 Results from PXS-4728A, a Selective SSAO/V AP-1 Inhibitor, for 1-18 the Treatment of Non-Alcoholic Steatohepatitis," *Journal of Hepatology* 62:s274-s275.

Wang, Y. et al. (Apr. 20, 2016, e-pub. Apr. 4, 2016). "Enantioselective CuH-Catalyzed Hydroallylation of Vinylarenes," *Journal of the American Chemical Society* 138(15):5024-5027.

International Preliminary Report on Patentability dated Feb. 21, 2019, for Patent Application No. PCT/CN2016/094833, filed Aug. 12, 2016, 7 pages.

International Preliminary Report on Patentability dated Feb. 21, 2019, for Patent Application No. PCT/CN2017/095999, filed Aug. 12, 2016, 6 pages.

International Search Report and Written Opinion dated Apr. 20, 2018, for Patent Application No. PCT/US2018/017152, 8 pages.

International Search Report and Written Opinion of the International Searching Authority, dated Mar. 29, 2018, for Patent Application No. PCT/CN2017/000157, 8 pages.

International Search Report and Written Opinion dated Nov. 13, 2017, for Patent Application No. PCT/CN2017/095999, 8 pages.

International Search Report and Written Opinion of the International Searching Authority, dated May 16, 2017, for PCT Patent Application No. PCT/CN2016/094833, 10 pages.

International Search Report and Written Opinion of the International Searching Authority, dated Nov. 22, 2018, for PCT Patent Application No. PCT/CN2017/117791, 8 pages.

U.S. Appl. No. 16/356,882, filed Mar. 18, 2019, for David A. Coates et al. (Copy not attached) (U.S. Patent Application is not submitted herewith pursuant to the waiver of 37 C.F.R § 1.98(a)(2)(iii) issued by the Office on Sep. 21, 2004.).

*Primary Examiner* — Kamal A Saeed
(74) *Attorney, Agent, or Firm* — Morrison and Foerster LLP

(57) ABSTRACT

The present invention provides compounds of the formula below pharmaceutically acceptable salts of the compounds, methods of treating patients for liver disease, and processes for preparing the compounds.

19 Claims, No Drawings

AMINO PYRIMIDINE COMPOUNDS USEFUL AS SSAO INHIBITORS

CROSS REFERENCE TO RELATED APPLICATIONS

This application is a continuation of U.S. patent application Ser. No. 16/012,140, filed Jun. 19, 2018, which is a continuation of International Application No. PCT/US2018/017152, filed Feb. 7, 2018, which claims priority benefit of International Application No. PCT/CN2017/000157, filed Feb. 14, 2017, and International Application No. PCT/CN2017/117791, filed Dec. 21, 2017, the disclosures of each of which are incorporated herein by reference.

This invention relates to amino pyrimidine compounds, pharmaceutically acceptable salts of the compounds, and therapeutic uses of the compounds and their salts.

Semicarbazide-sensitive amino oxidase/vascular adhesion protein-1 (SSAO/VAP-1) exists both as a membrane-bound isoform and a plasma soluble isoform. It is predominantly expressed from endothelial cell surfaces, vascular smooth muscle and adipose cells. SSAO/VAP-1 participates in many cellular processes including glucose disposition, inflammation responses and associated pain, and leukocyte recruitment.

High activity levels of this enzyme are associated with diabetes, atherosclerosis, strokes, chronic kidney disease, and Alzheimer's disease, among other disorders. SSAO/VAP-1 has been implicated in the pathogenesis of liver diseases such as fatty liver disease. (Weston C. J., et al., J. Neural. Transm., 2011, 118, 1055.) Fatty liver disease (FLD) encompasses a spectrum of disease states characterized by excessive accumulation of fat in the liver often accompanied with inflammation. FLD can lead to non-alcoholic fatty liver disease (NAFLD), which is characterized by insulin resistance. If untreated NAFLD, can progress to a persistent inflammatory response or non-alcoholic steatohepatitis (NASH), progressive liver fibrosis, and eventually to cirrhosis. Currently there is a need to provide alternative treatment therapies for liver diseases such as NAFLD and/or NASH.

It is thought that a SSAO/VAP-1 inhibitor will reduce liver inflammation and fibrosis and thereby provide a treatment for liver diseases, in particular, a treatment for NAFLD and/or NASH. In addition, since activation of SSAO/VAP-1 has been implicated in inflammation and associated pain, inhibition of SSAA/VAP-1 enzyme may be useful in treating pain, and in particular, pain associated with osteoarthritis. (Luis M. et al., J of Pharm and Experimental Therapeutics, 2005, 315, 553.)

U.S. Pat. No. 8,426,587 discloses haloallylamine compounds useful as SSAO/VAP1 inhibitors.

Currently, there is no approved drugs for the treatment for NASH; the standard of care for NASH consists of diet control and/or life style changes. In addition, the current standard of care for pain is dominated by nonsteroidal anti-inflammatory drugs (NSAIDS) and opiates. Both classes of drugs are recommended for short term use only. It is desirable to have more treatment options to control pain, in particular chronic pain. The present invention provides compounds that inhibit the SSAO/VAP-1 enzyme and which may address one or more of these needs.

The present invention provides a compound of the Formula 1 below:

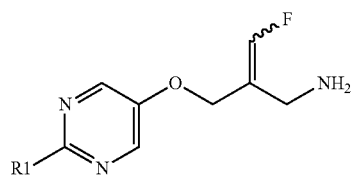

where R1 is selected from:

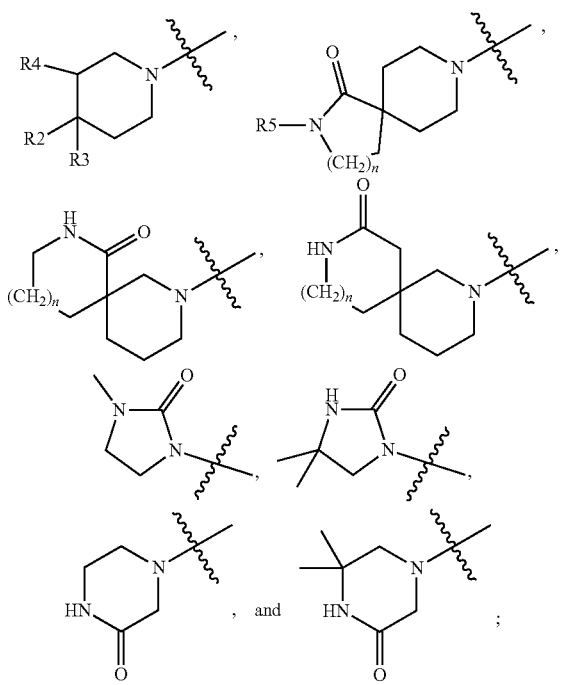

R2 is selected from: H, —C(O)NH$_2$, —C(O)NH(CH$_3$), —C(O)N(CH$_3$)$_2$,

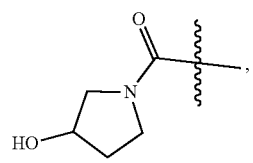

and

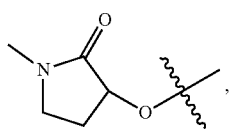 [SMILES: *OC1CCN(C)C1=O]

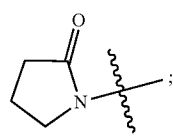 [SMILES: *N1CCCC1=O]

R3 is H or CH₃, R4 is H or

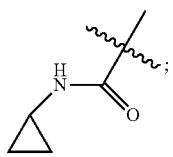 [SMILES: *C(=O)NC1CC1]

R5 is selected from: H, —C$_{1-4}$alkyl, —C$_{3-4}$ cycloalkyl, —CH$_2$—C$_{3-4}$ cycloalkyl; and n is 1 or 2; or a pharmaceutically acceptable salt thereof.

The bond to fluorine illustrated as ⁓ indicates that the fluorine atom and the methoxypyrimidine group can be either Z (zusammen, together) or E (entgegen, opposite) relative to each other. (See Brecher, J., et al., "Graphical Representation of Stereochemical Configuration", Pure and Appl. Chem, 2006, 78(10) 1897, at 1959.) The structure illustrated by Formula 1 includes compounds exhibiting the Z stereochemical configuration or the E stereochemical configuration about the double bond; or a mixture of compounds individually exhibiting the Z or E stereochemical configuration. Preferred compounds of the invention have the E stereochemical configuration about that double bond.

The present invention also provides a compound of Formula 2:

where R1 is selected from:

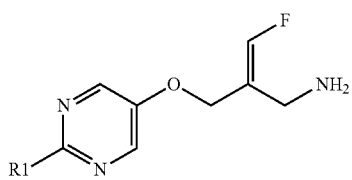

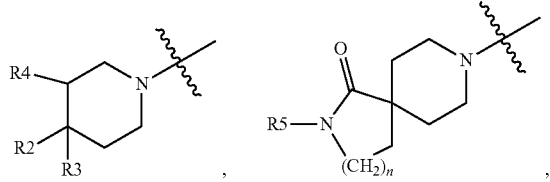

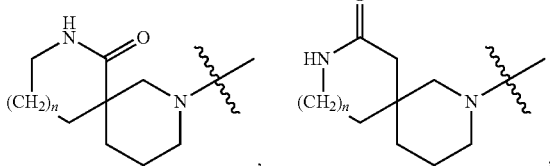

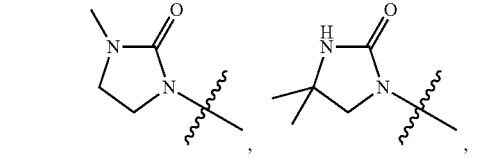

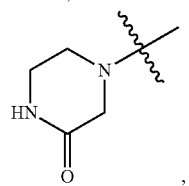

and

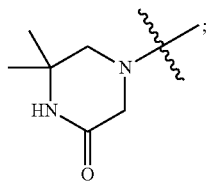 [SMILES: *N1CC(=O)NC(C)(C)C1]

R2 is selected from: H, —C(O)NH$_2$, —C(O)NH(CH$_3$), —C(O)N(CH$_3$)$_2$,

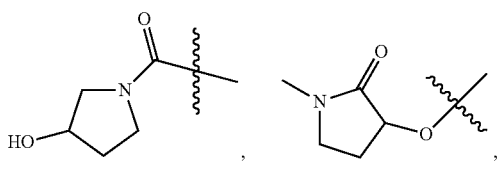

and

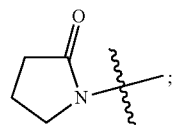 [SMILES: *N1CCCC1=O]

R3 is H or CH₃; R4 is H or

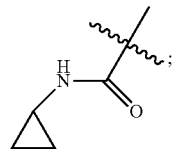 [SMILES: *C(=O)NC1CC1]

R5 is selected from: H, —C$_{1-4}$alkyl, —C$_{3-4}$ cycloalkyl, and —CH$_2$—C$_{3-4}$ cycloalkyl; and n is 1 or 2; or a pharmaceutically acceptable salt thereof.

In another form, the present invention provides a compound according to Formula 1 or 2 where R1 is selected from:

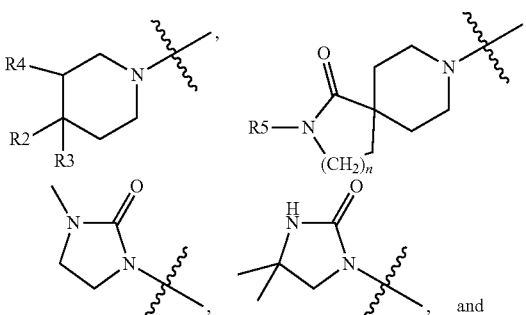

and

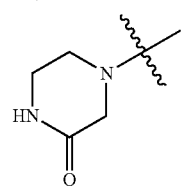

and where R2, R3, R4, R5, and n are as provided above; or a pharmaceutically acceptable salt thereof. In one preferred embodiment, R1 is

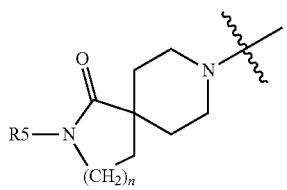

and R5, and n are as provided above. In another preferred embodiment, R1 is

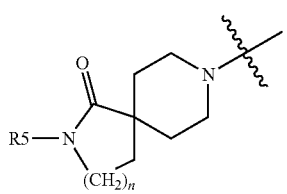

and R5 is selected from: H, —CH₃,

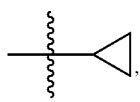

and

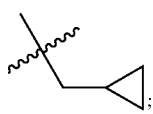 [SMILES: *CC1CC1]

more preferably, R5 is —CH₃.

In another form, the present invention provides a compound according to Formula 1 or 2 where R1 is

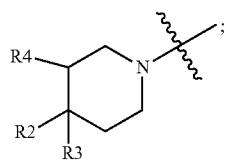

R2 is selected from: H, —C(O)NH₂, —C(O)NH(CH₃), —C(O)N(CH₃)₂,

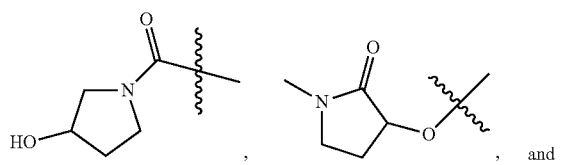, and

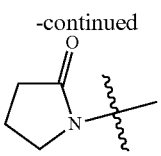;

and R3, and R4 are as provided above, or a pharmaceutically acceptable salt thereof. In one preferred embodiment, R3 is H and R4 is provided as above, or a pharmaceutically acceptable salt thereof. In another preferred embodiment, R3 is H and R4 is H.

In another form, the present invention provides a compound according to Formula 1 or 2 where R1 is

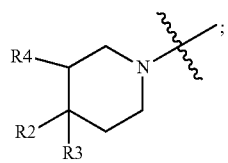

R4 is

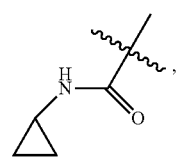 [SMILES: *C(=O)NC1CC1], and R2 and R3 are as provided above, or a pharmaceutically acceptable salt thereof. More preferable, R2 and R3 are both H.

In another form, the present invention provides a compound according to Formula 3 below:

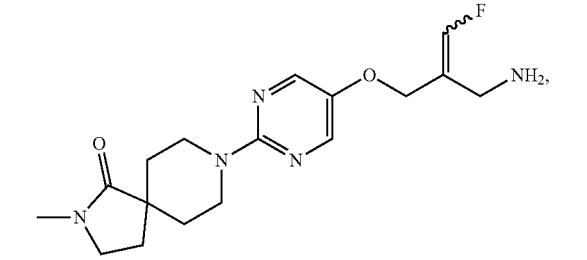

3 or a pharmaceutically acceptable salt thereof.

In yet another form, the present invention provides a compound of Formula 4 below:

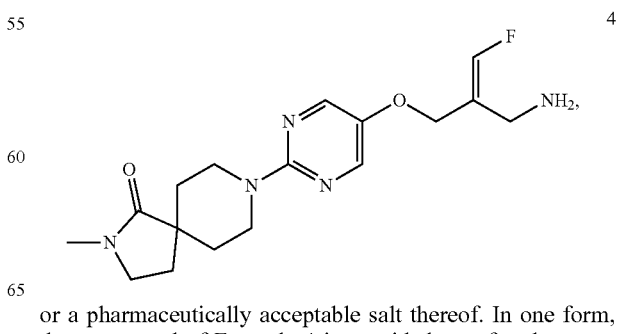

4 or a pharmaceutically acceptable salt thereof. In one form, the compound of Formula 4 is provided as a free base.

In another form, the compound of Formula 4 is provided as a pharmaceutically acceptable salt. Preferably the compound of Formula 4 is provided as a mono or di hydrochloride addition salt.

In another form, the present invention provides a pharmaceutical composition comprising a compound according to any one of Formulae 1 to 4, or a pharmaceutically acceptable salt thereof, and a pharmaceutically acceptable carrier, diluent or excipient.

The pharmaceutical composition can be used in the treatment of a patient suffering from a liver disorder.

In another form, the present invention provides a method of treating a patient in need there of for a liver disorder. The method comprises administering to the patient an effective amount of a compound according to Formulae 1 to 4, or a pharmaceutically acceptable salt thereof. In certain embodiments, the method comprises treating a patient in need of treatment for a liver disorder where the liver disorder is selected from: liver fibrosis, alcohol induced fibrosis, alcoholic steatosis, non-alcoholic fatty liver disease (NAFLD), and non-alcoholic steatohepatitis (NASH). In a particularly preferred embodiment, the method comprises treating a patient in need for treatment of NASH.

Preferably the method comprises administering an effective amount of a compound of Formula 4, or a pharmaceutically acceptable salt thereof, for the treatment of NASH.

In another form, the present invention provides a compound according to any one of Formulae 1 to 4, or a pharmaceutically acceptable salt thereof, for use in therapy. In preferred embodiments, the present invention provides a compound according to any one of Formulae 1 to 4, or a pharmaceutically acceptable salt thereof, for the treatment of a liver disorder. The liver disorder may be selected from: liver fibrosis, alcohol induced fibrosis, alcoholic steatosis, NAFLD, and NASH. In one embodiment, the therapy is for the treatment of liver fibrosis. In another embodiment, the therapy is for NAFLD. In still yet another embodiment, the therapy is for NASH.

In yet another form, the present invention provides for the use of a compound according to Formulae 1 to 4, or a pharmaceutically acceptable salt thereof in the manufacture of a medicament for the treatment of a liver disorder. In preferred embodiments, the liver disorder is selected from: liver fibrosis, alcohol induced fibrosis, alcoholic steatosis, NAFLD, and NASH.

The term "pharmaceutically-acceptable salt" as used herein refers a salt of a compound of the invention considered to be acceptable for clinical and/or veterinary use. Examples of pharmaceutically acceptable salts and common methodology for preparing them can be found in "Handbook of Pharmaceutical Salts: Properties, Selection and Use" P. Stahl, et al., 2nd Revised Edition, Wiley-VCH, 2011 and S. M. Berge, et al., "Pharmaceutical Salts", Journal of Pharmaceutical Sciences, 1977, 66(1), 1-19.

The pharmaceutical compositions for the present invention may be prepared using pharmaceutically acceptable additives. The term "pharmaceutically acceptable additive(s)" as used herein for the pharmaceutical compositions, refers to one or more carriers, diluents, and excipients that are compatible with the other additives of the compositions or formulations and not deleterious to the patient. Examples of pharmaceutical compositions and processes for their preparation can be found in "Remington: The Science and Practice of Pharmacy", Loyd, V., et al. Eds., 22$^{nd}$ Ed., Mack Publishing Co., 2012.

As used herein, the term "effective amount" refers to an amount that is a dosage, which is effective in treating a disorder, such as a liver disease including liver inflammation, fibrosis, and steatohepatitis. The attending physician, as one skilled in the art, can readily determine an effective amount by the use of conventional techniques and by observing results obtained under analogous circumstances. Factors considered in the determination of an effective amount or dose of a compound include: whether the compound or its salt will be administered; the co-administration of other agents, if used; the species of mammal; its size, age, and general health; the degree of involvement or the severity of the disorder; the response of the individual patient; the mode of administration; the bioavailability characteristics of the preparation administered; the dose regimen selected; the use of other concomitant medication; and other relevant circumstances.

As used herein, the terms "treating", "to treat", or "treatment", includes slowing, reducing, or reversing the progression or severity of an existing symptom, disorder, condition, or disease, which can include treating liver disease, such as, liver inflammation, fibrosis, and steatohepatitis.

As used herein, the term "patient" refers to a mammal, preferably the patient is a human or companion mammal, such as, a dog or cat.

A treating physician, veterinarian, or other medical person will be able to determine an effective amount of the compound for treatment of a patient in need. Preferred pharmaceutical compositions can be formulated as a tablet or capsule for oral administration, a solution for oral administration or an injectable solution. The tablet, capsule, or solution can include a compound of the present invention in an amount effective for treating a patient in need of treatment.

The abbreviations used herein are defined according to Daub G. H., et al., "The Use of Acronyms in Organic Chemistry" Aldrichimica Acta, 1984, 17(1), 6-23. Other abbreviations are defined as follows: "Boc" refers to tert-butoxycarbonyl; "DBAD" refers to dibenzyl azodicarboxylate; "DCM" refers to dichloromethane; "DIPEA" refers to N,N-diisopropylethylamine; "DMF" refers to dimethylformamide; "DMSO" refers to dimethylsulfoxide; "EDTA" refers to ethylenediaminetetraacetic acid; "EGTA" refers to ethylene glycol tetraacetic acid; "ES/MS" refers to electrospray mass spectroscopy; "EtOAc" refers to ethyl acetate; "EtOH" refers to ethanol or ethyl alcohol; "HATU" refers to (dimethylamino)-N,N-dimethyl(3H-[1,2,3]triazolo[4,5-b]pyridin-3-yloxy)methaniminium hexafluorophosphate; "HEPES" refers to 4-(2-hydroxyethyl)-1-piperazineethanesulfonic acid; "hr or hrs" refers to hour or hours; "IC$_{50}$" refers to the concentration of an agent which produces 50% of the maximal inhibitory response possible for that agent (relative IC$_{50}$), or the concentration of an agent which produces 50% inhibition of the target activity compared to placebo control (absolute IC$_{50}$); "IU" refers to International units; LCMS" refers to liquid chromatography mass spectrometry; "MAOa and MAOb" refers to monoamine oxidase a and b isoform, respectively; "MeOH" refers to methyl alcohol or methanol; "min" or mins refers to minutes; "MTBE" refers to methyl t-butyl ether; NASH" refers to Nonalcoholic steatohepatitis; "NMP" refers to N-methylpyrrolidone or 1-methyl-2-pyrrolidinone; PE refers to petroleum ether; t$_{(R)}$=retention time; "sat" refers to a saturated solution; "SSAO" refers to semicarbazide-sensitive amine oxidase; "hSSAO" refers to human SSAO; and "TG" refers to triglyceride; "THF" refers to tetrahydrofuran.

In the preparations described herein the hydroxyl and amino functionalities can be protected to facilitate the synthesis of the compounds described herein. Examples of protecting functionalities can be found in "Greene's Protective Groups in Organic Synthesis," Wuts, P. G. M., et al., Eds. 5th Ed., John Wiley and Sons, 2014. Other functional groups that can be readily converted to the hydroxyl group or the amino group can be used. Such functional groups, preparations, and transformations of these groups can be found in "Comprehensive Organic Transformations: A Guide to Functional Group Preparations" by Larock. R. C., Wiley VCH, 1999 and in "March's Advanced Organic Chemistry: Reactions, Mechanisms and Structure," Smith, M. B., Ed., 7th Ed., Wiley-Interscience, 2013.

The compounds of the present invention, or salts thereof, may be prepared by a variety of procedures some of which are illustrated in the Schemes, Preparations, and Examples below. The products of each step in the Schemes below can be recovered by conventional methods including extraction, evaporation, precipitation, chromatography, filtration, trituration, and crystallization. Furthermore, individual isomers, enantiomers, and diastereomers may be separated or resolved by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "Stereochemistry of Organic Compounds", Wiley-Interscience, 1994). In the Schemes below, all substituents unless otherwise indicated, are as previously defined. The reagents and starting materials are readily available to one of ordinary skill in the art.

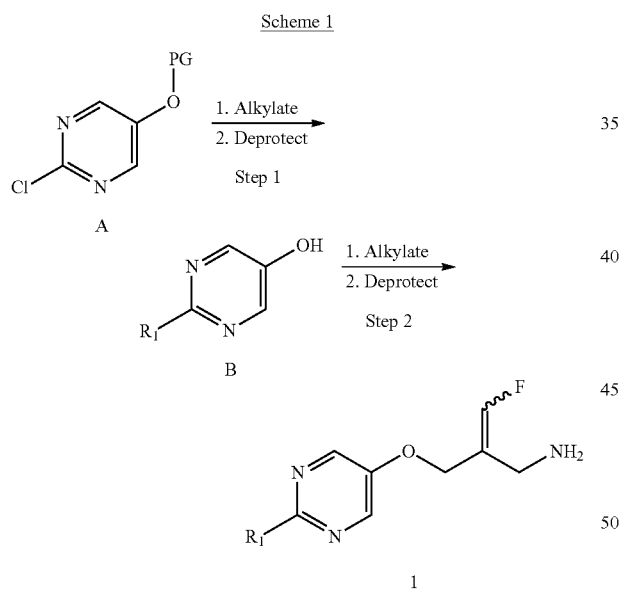

PG is a Protecting Group

Scheme 1 depicts a generic synthesis of compounds of Formula 1, where "PG" is a protecting group for the hydroxyl group. Specifically in Step 1, substep 1, the chloro of compound A can be replaced with the nitrogen of an R1 substituted cyclic amine to give compound B. In Step 1, substep 2 deprotection of the hydroxyl group can be accomplished by a variety of methods dependent upon the specific protecting group. In step 2, substep 1, the resulting hydroxyl of compound B can be alkylated with a suitably protected amine 2-bromo-3-fluoro-propyl-2-en-amine, to give compounds of Formula 1. The alkylation typically can be accomplished under basic conditions. The protected amine can be deprotected to give compounds of Formula 1.

PREPARATIONS AND EXAMPLES

The following Preparations and Examples further illustrate the invention and represent typical synthesis of the compounds of the invention.

Preparation 1 tert-Butyl 4-(5-bromo-2-pyridyl)-2-oxo-piperazine-1-carboxylate

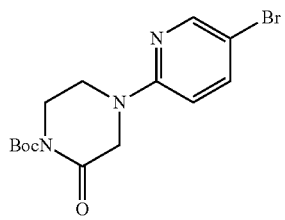

Add triethylamine (2.4 mL, 17 mmol), DMAP (160 mg, 1.30 mmol) and tert-butoxycarbonyl tert-butyl carbonate (1.87 g, 1.1 equiv., 8.59 mmol) to a solution of 4-(5-bromo-2-pyridyl)piperazin-2-one (2.00 g, 7.81 mmol) in DCM (45 mL). Stir the reaction mixture at 25° C. for 3 days to give a yellow suspension. Add DCM (50 mL) to the reaction and wash the mixture with brine (5×50 mL). Concentrate the organic layer to give the crude product as a yellow solid. Subject the material to silica gel chromatography eluting with a gradient of 0 to 50% EtOAc in PE to give the title compound (1.57 g, 55%) as white solid.

Preparation 2

Tert-Butyl 2-oxo-4-[5-(4,4,5,5-tetramethyl-1,3,2-dioxaborolan-2-yl)-2-pyridyl]piperazine-1-carboxylate

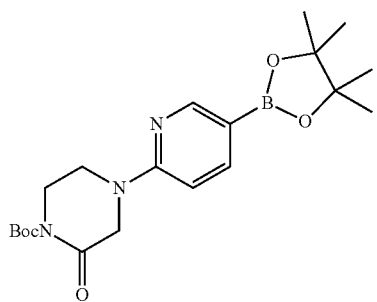 [SMILES: CC(C)(C)OC(=O)N1CCN(c2ccc(B3OC(C)(C)C(C)(C)O3)cn2)CC1=O]

Add to a suspension of tert-butyl 4-(5-bromo-2-pyridyl)-2-oxo-piperazine-1-carboxylate (1.57 g, 4.41 mmol), 4,4,5,5-tetramethyl-2-(4,4,5,5-tetramethyl-1,3,2-dioxaborolan-2-yl)-1,3,2-dioxaborolane (1.23 g, 1.1 equiv., 4.85 mmol) and potassium acetate (1.29 g, 3.00 equiv., 13.2 mmol) in 1,4-dioxane (30 mL) Pd(dppf)Cl$_2$) (0.32 g, 0.1 equiv., 0.441 mmol) at 25° C. Degas the reaction mixture while stirring at 100° C. under N$_2$ for 1 hr. Filter the reaction mixture and concentrate the filtrate to give the crude product as a yellow oil. Subject the material to silica gel chromatograph eluting with a gradient of 0 to 50% EtOAc in PE to give the title compound (1.70 g, 96%) as pale yellow solid.

Preparation 3 tert-Butyl 4-(5-hydroxy-2-pyridyl)-2-oxo-piperazine-1-carboxylate

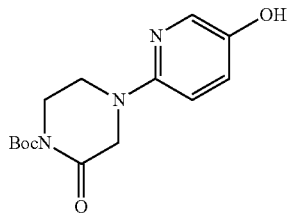 [SMILES: CC(C)(C)OC(=O)N1CCN(c2ccc(O)cn2)CC1=O]

Add sodium hydroxide (aq. 2 mL, 1 µM) and hydrogen peroxide (aq. 2 mL, 30 mass %) to a suspension of tert-butyl 2-oxo-4-[5-(4,4,5,5-tetramethyl-1,3,2-dioxaborolan-2-yl)-2-pyridyl]piperazine-1-carboxylate (500 mg, 1.24 mmol) in THF (5 mL, 61.6 mmol) at 0° C. Stir the reaction mixture at 25° C. for 2 hrs. Quench the reaction with saturated $Na_2SO_3$ solution and adjust the pH to 6-7 with 1 M HCl. Extract the mixture with EtOAc (3×20 mL) and concentrate the combined organic extracts to give a crude product as a yellow oil. Subject the crude product to silica gel chromatography eluting with a gradient of 0 to 70% of EtOAc in PE to give the title compound (120 mg, 33%) as yellow solid. LCMS (m/z): 294.0 $[M+H]^+$.

Preparation 4

1-Methyl-3-(4-pyridyloxy)pyrrolidin-2-one

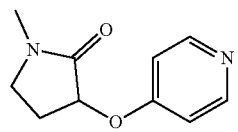

Dropwise add a solution of DBAD (3.06 g, 13.0 mmol) in THF (10 mL) to a solution of 3-hydroxy-1-methyl-pyrrolidin-2-one (500 mg, 4.34 mmol), pyridin-4-ol (0.826 g, 8.69 mmol) and (n-butyl)$_3$P (2.72 g, 13.0 mmol) in DCM (9 mL) and THF (15 mL) at 0° C. and stir the reaction mixture at room temperature for 4 hrs. Concentrate the reaction mixture under vacuum and purify the residue by silica gel flash chromatography eluting with a gradient of 0.5-10% MeOH in DCM to give the title compound (300 mg, 32% yield) as a light yellow oil. LCMS (m/z): 193.0 $[M+H]^+$, $^1$H NMR (400 MHz, CDCl$_3$) δ 8.50-8.35 (m, 2H), 7.00-6.87 (m, 2H), 4.94 (dd, J=6.0, 7.6 Hz, 1H), 3.56-3.46 (m, 1H), 3.44-3.32 (m, 1H), 2.93 (s, 3H), 2.63-2.50 (m, 1H), 2.21-2.09 (m, 1H).

Preparation 5

3-(1-Benzylpyridin-1-ium-4-yl)oxy-1-methyl-pyrrolidin-2-one bromide

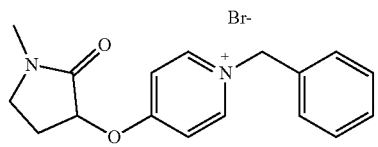

Add bromomethylbenzene (0.534 g, 3.12 mmol) to a mixture of 1-methyl-3-(4-pyridyloxy)pyrrolidin-2-one (5, 300 mg, 1.56 mmol) in DMF (8.0 mL) and warm the reaction mixture to 55° C. for 16 hrs. Concentrate the reaction mixture under vacuum, dilute with water (20 mL) and extract with EtOAc (2×10 mL). Concentrate the aqueous layer under vacuum to give the title compound (450 mg, 71.4%) as a white solid. $^1$H NMR (400 MHz, d$_6$-DMSO) δ 9.04 (d, J=7.2 Hz, 2H), 7.75 (d, J=7.6 Hz, 2H), 7.56-7.48 (m, 2H), 7.47-7.33 (m, 3H), 5.72 (s, 2H), 5.61 (t, J=8.0 Hz, 1H), 3.42-3.37 (m, 5H), 2.70-2.58 (m, 1H), 2.17-2.00 (m, 1H)

Preparation 6

3-[(1-Benzyl-3,6-dihydro-2H-pyridin-4-yl)oxy]-1-methyl-pyrrolidin-2-one

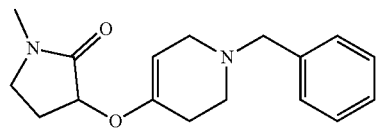 [SMILES: CN1CCC(OC2=CCN(Cc3ccccc3)CC2)C1=O]

Add NaBH$_4$ (212 mg, 5.58 mmol) to a solution of 3-(1-benzylpyridin-1-ium-4-yl)oxy-1-methyl-pyrrolidin-2-one bromide (450 mg, 1.12 mmol) in MeOH (8.0 mL) at 0° C. and stir the reaction mixture at 0° C. for 10 min. Dilute the reaction mixture with EtOAc (40 mL) and wash with NaHCO$_3$ (sat.aq.) (30 mL) and brine (30 mL). Dry the organic layer over anhydrous Na$_2$SO$_4$, filter, and concentrate the filtrate under vacuum. Subject the crude product to silica gel flash chromatography eluting with a gradient of 0-1% MeOH in DCM to give the title compound (120 mg, 36%) as a colorless gum. LCMS (m/z): 287.1 $[M+H]^+$, H NMR (400 MHz, CDCl$_3$) b 7.45-7.14 (m, 5H), 4.71 (t, J=3.2 Hz, 1H), 4.62-4.50 (m, 1H), 3.74-3.50 (m, 2H), 3.50-3.40 (m, 1H), 3.40-3.25 (m, 1H), 3.18-3.06 (m, 1H), 3.05-2.95 (m, 1H), 2.89 (s, 3H), 2.75-2.65 (m, 1H), 2.55-2.47 (m, 1H), 2.43-2.30 (m, 1H), 2.25-2.15 (m, 2H), 2.06-1.94 (m, 1H)

Preparation 7

1-Methyl-3-(4-piperidyloxy)pyrrolidin-2-one

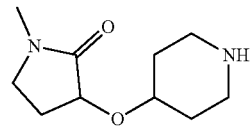

Add palladium on carbon (50% water, 10% w, 20.0 mg) to a solution of 3-[(1-benzyl-3,6-dihydro-2H-pyridin-4-yl)oxy]-1-methyl-pyrrolidin-2-one (120 mg, 0.40 mmol) in EtOH (6.0 mL) and stir the reaction mixture at room temperature under a hydrogen atmosphere for 5 hrs. Filter the reaction mixture through diatomaceous earth and concentrate the filtrate under vacuum to give the title compound (85.0 mg, 96.9%) as a colorless gum. $^1$H NMR (400 MHz, CDCl$_3$) δ 4.20-4.10 (m, 1H), 3.90-3.80 (m, 1H), 3.45-3.35 (m, 1H), 3.30-3.18 (m, 1H), 3.14-3.04 (m, 2H), 2.85 (s, 3H), 2.66-2.55 (m, 2H), 2.36-2.28 (m, 1H), 1.98-1.90 (m, 2H), 1.55-1.35 (m, 2H)

Preparation 8 tert-Butyl 2-cyclopropyl-1-oxo-2,8-diazaspiro[4.5]decane-8-carboxylate

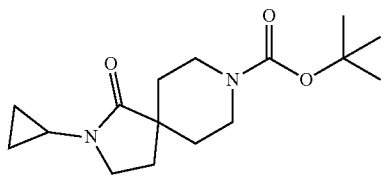 [SMILES: CC(C)(C)OC(=O)N1CCC2(CC1)CCN(C1CC1)C2=O]

Combine tert-butyl 1-oxo-2,8-diazaspiro[4.5]decane-8-carboxylate (161 mg, 0.60 mmol), copper(II) acetate (110 mg, 0.61 mmol) and cesium carbonate (98 mg, 0.30 mmol). Then add pyridine (145 mg, 1.83 mmol), 2-cyclopropyl-4,4,5,5-tetramethyl-1,3,2-dioxaborolane (203 mg, 1.21 mmol) and toluene (1.2 mL) via syringe. Heat the mixture to 110° C. for 64 hrs. Wash the mixture with EtOAc and filter through diatomaceous earth. Concentrate the filtrate and subject the residue to silica gel flash chromatography eluting with 50% EtOAc in hexanes to give the title compound as a light yellow oil. LCMS (m/z): 317.3 [M+Na]$^+$

Preparation 9

2-Cyclopropyl-2,8-diazaspiro[4.5]decan-1-one Hydrochloride

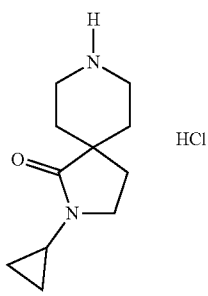 [SMILES: O=C1N(C2CC2)CCC12CCNCC2 ; Cl]

Dissolve tert-butyl 2-cyclopropyl-1-oxo-2,8-diazaspiro[4.5]decane-8-carboxylate (172 mg, 0.555 mmol) in HCl in MeOH (6.0 mL, 3 mmol, 0.5 mmol/mL) and heat to 80° C. for 50 min. Concentrate the mixture under vacuum to give the title compound as a pale brown oil which is used without further purification. LCMS (m/z): 195.3 [M+H]

Preparation 10

O1-tert-Butyl 04-methyl 4-(2-bromoethyl)piperidine-1,4-dicarboxylate

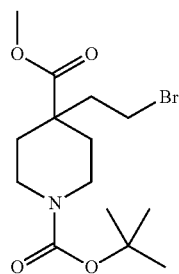 [SMILES: COC(=O)C1(CCBr)CCN(C(=O)OC(C)(C)C)CC1]

Add lithium diisopropylamide in hexanes (9.70 mL, 19.396 mmol, 2 mol/L) dropwise at −78° C. under N$_2$ to a solution of O1-tert-butyl O4-methyl piperidine-1,4-dicarboxylate (3.146 g, 12.93 mmol) in THF (45 mL). Stir the resulting mixture at −78° C. for 30 min and then add 1,2-dibromoethane (2.23 mL, 25.861 mmol). Allow the resultant mixture to warm to room temperature and stir for 1 hr. Quench the reaction with sat. NH$_4$Cl aq. (20 mL), and extract with EtOAc (2×30 mL). Combine the organic extracts, dry over Na$_2$SO$_4$, filter, and concentrate to dryness. Purify the crude material via silica gel flash chromatography eluting with 20% EtOAc in hexanes to give the title compound (0.698 g, 15%) as yellowish oil. LCMS (m/z): ($^{79}$Br/$^{81}$Br) 372.2/374.2 [M+Na]$^+$

Preparation 11 tert-Butyl 2-tert-butyl-1-oxo-2,8-diazaspiro[4.5]decane-8-carboxylate

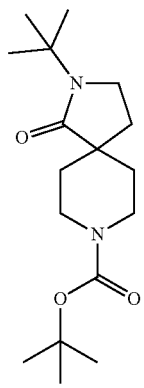 [SMILES: CC(C)(C)OC(=O)N1CCC2(CC1)CCN(C(C)(C)C)C2=O]

Dissolve O1-tert-butyl O4-methyl 4-(2-bromoethyl)piperidine-1,4-dicarboxylate (698 mg, 1.89 mmol) in MeOH (5 mL) and add 2-methylpropan-2-amine (1.59 mL, 15.1 mmol). Heat the solution to 120° C. via microwave irradiation for 16 hrs. Concentrate the solution, then purify the residue via silica gel flash chromatography eluting with 25% EtOAc in hexanes to give the title compound (74 mg, 11%) as light yellow oil. LCMS (m/z): 333.3 [M+Na]$^+$

Preparation 12

2-tert-Butyl-2,8-diazaspiro[4.5]decan-1-one Hydrochloride

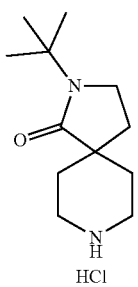

Dissolve tert-butyl 2-tert-butyl-1-oxo-2,8-diazaspiro[4.5]decane-8-carboxylate (74 mg, 0.21 mmol) in HCl in MeOH (5 mL, 2.5 mmol, 0.50 mmol/mL) and heat to 80° C. via microwave irradiation for 5 min. Concentrate the solution to give the title compound (56 mg, 95%) as light yellow oil. LCMS (m/z): 211.2 [M+H]+

Preparation 13

2-Methyl-2,8-diazaspiro[4.5]decan-1-one Hydrochloride

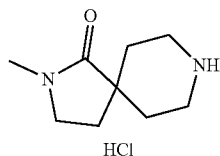

Cool tert-butyl 2-methyl-1-oxo-2,8-diazaspiro[4.5]decane-8-carboxylate (45.2 g, 168 mmol) to 0° C. Add HCl in MeOH (250 mL, 4.0 µM) and stir the solution vigorously for 30 minutes. Warm the mixture to room temperature, stir for 5 hrs, and then concentrate to dryness to give the title compound (34.6 g, 98.4%) as a pale yellow solid. ES/MS (m/z) 169.2 (M+H).

Preparation 14 tert-Butyl N-[(E)-2-[(2-chloropyrimidin-5-yl)oxymethyl]-3-fluoro-allyl]carbamate

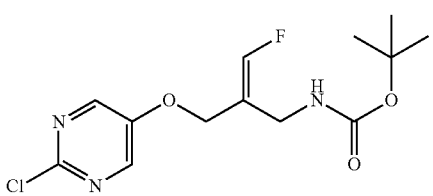 [SMILES: CC(C)(C)OC(=O)NC/C(=C\F)COc1cnc(Cl)nc1]

Add potassium carbonate (1.126 g, 8.14 mmol) to a solution of 2-chloropyrimidin-5-ol (501 mg, 3.84 mmol) and tert-butyl N-[(E)-2-(bromomethyl)-3-fluoro-allyl]carbamate (507 mg, 1.89 mmol) in DMF (10 mL) and stir the resulting mixture at room temperature overnight. Quench the reaction by adding water and EtOAc and extract the aqueous phase with EtOAc (3×50 mL). Combine the organic extracts, dry the solution over Na₂SO₄, filter, and concentrate the filtrate under vacuum. Subject the material to silica gel flash chromatography with EtOAc in hexanes to give the title compound as a white solid (658 mg, 87%). LCMS (ESI): m/s 340.2 [M+Na]+.

Preparation 15

8-(5-Benzyloxypyrimidin-2-yl)-2,8-diazaspiro[4.5]decan-1-one

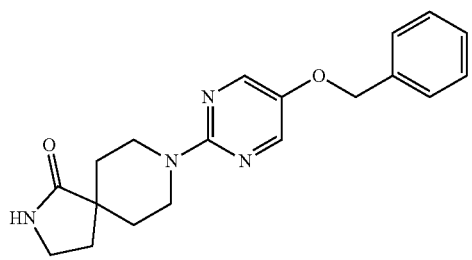 [SMILES: O=C1NCCC12CCN(c1ncc(OCc3ccccc3)cn1)CC2]

Add DIPEA (1.7 g, 13 mmol) and 5-benzyloxy-2-chloropyrimidine (0.61 g, 2.8 mmol) to a mixture of 2-methyl-2,8-diazaspiro[4.5]decan-1-one hydrochloride (0.50 g, 2.6 mmol) in NMP (10 mL). Stir the reaction mixture at 100° C. for 20 hrs. Then dilute the reaction mixture with water (40 mL) and extract with EtOAc (2×20 mL). Combine the organic extracts; wash with brine (3×20 mL); dry over anhydrous Na₂SO₄; filter; and concentrate the filtrate under vacuum to provide a residue. Subject the residue to flash chromatography on silica gel eluting with a gradient of 0-1% MeOH in DCM to give the title compound (0.39 g, 42%) as a light yellow solid. ¹H NMR (400 MHz, CDCl₃) δ 8.11 (s, 2H), 7.45-7.30 (m, 5H), 5.79 (s, 1H), 5.02 (s, 2H), 4.55-4.45 (m, 2H), 3.38 (t, J 6.8 Hz, 2H), 3.21-3.10 (m, 2H), 2.15 (t, J=6.8 Hz, 2H), 1.98-1.85 (m, 2H), 1.55-1.43 (m, 2H).

Preparation 16

1-(5-Benzyloxypyrimidin-2-yl)piperidine-4-carboxamide

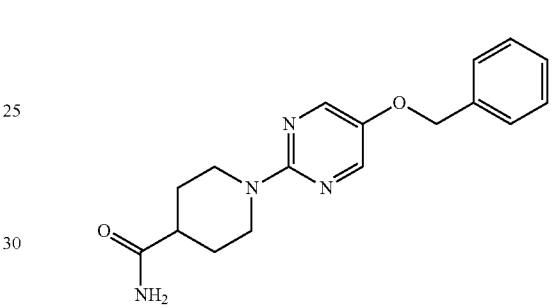

Stir a mixture of 5-benzyloxy-2-chloro-pyrimidine (400 mg, 1.81 mmol), piperidine-4-carboxamide (0.28 g, 1.2 equiv., 2.18 mmol) and DIPEA (2.0 equiv., 3.63 mmol) in DMF (6 mL) at 100° C. under N₂ for 17 hrs. Pour the reaction mixture into water (60 mL) and filter. Wash the filter cake with EtOAc (30 mL) and stir the material for 0.5 hr. Filter the solution and dry the filter cake under reduced pressure to give the title compound (310 mg, 49%) as a pink solid. ¹H NMR: (400 MHz, CD₃OD) δ 8.13 (s, 2H), 7.47-7.28 (m, 5H), 5.07 (s, 2H), 4.67-4.60 (m, 2H), 2.95-2.84 (m, 2H), 2.50-2.40 (m, 1H), 1.85-1.75 (m, 2H), 1.68-1.60 (m, 2H).

Preparation 17

8-(5-Benzyloxypyrimidin-2-yl)-2-cyclopropyl-2,8-diazaspiro[4.5]decan-1-one

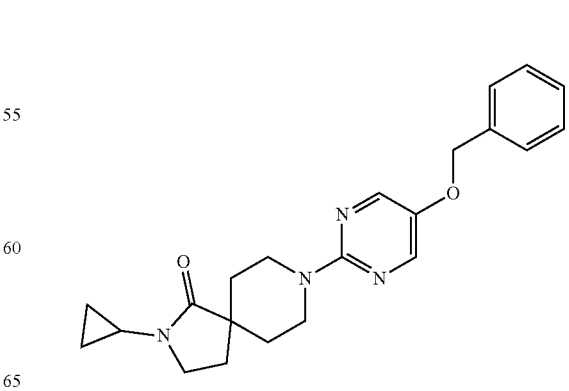

Add together 5-benzyloxy-2-chloro-pyrimidine (79 mg, 0.36 mmol) and potassium carbonate (164 mg, 1.19 mmol).

Dissolve 2-cyclopropyl-2,8-diazaspiro[4.5]decan-1-one; hydrochloride (72 mg, 0.30 mmol) in EtOH (3.0 mL) and add to the reaction mixture. Heat the reaction to 110° C. via microwave irradiation for 62 hrs. Dilute the mixture with EtOAc and filter the slurry through diatomaceous earth. Concentrate the filtrate and purify the crude mixture via silica gel flash chromatography eluting with 55% EtOAc in hexanes to give the title compound (40 mg, 35%) as white solid. LCMS (m/z): 379.2 [M+H]$^+$.

Preparation 18

8-(5-Benzyloxypyrimidin-2-yl)-2-tert-butyl-2,8-diazaspiro[4.5]decan-1-one

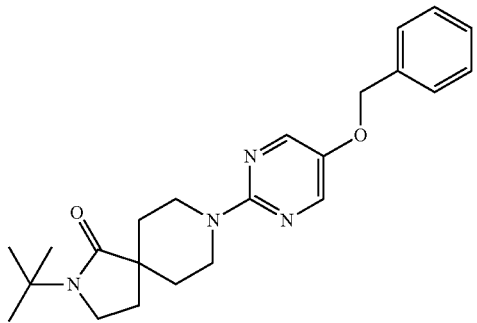 [SMILES: CC(C)(C)N1CCC2(CCN(c3ncc(OCc4ccccc4)cn3)CC2)C1=O]

Add NMP (1 mL) to 2-tert-butyl-2,8-diazaspiro[4.5]decan-1-one; hydrochloride (56 mg, 0.20 mmol), 5-benzyloxy-2-chloro-pyrimidine (54 mg, 0.25 mmol) and potassium carbonate (113 mg, 0.82 mmol). Heat the mixture to 120° C. via microwave irradiation for 16 hrs. Dilute the mixture with EtOAc and filtrate it through diatomaceous earth. Concentrate the filtrate to provide a residue and subject the residue to silica gel flash chromatography eluting with 25% EtOAc in hexanes to give the title compound (16 mg, 19% yield) as a white solid. LCMS (m/z): 395.3 [M+H]$^+$ Preparation 19

9-(5-Benzyloxypyrimidin-2-yl)-2,9-diazaspiro[5.5]undecan-1-one

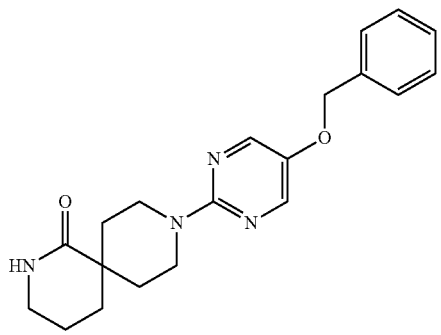 [SMILES: O=C1NCCCC12CCN(c1ncc(OCc3ccccc3)cn1)CC2]

Dissolve tert-butyl 1-oxo-2,9-diazaspiro[5.5]undecane-9-carboxylate (1.907 g, 6.96 mmol) in DCM (50 mL) and add trifluoroacetic acid (10 mL) at room temperature with stirring. Stir the resultant solution for 4 hrs. Concentrate the solution to give an intermediate 2,9-diazaspiro[5.5]undecan-1-one; 2,2,2-trifluoroacetic acid (2.096 g, 6.683 mmol) as a light yellow oil. Add to the crude mixture 5-benzyloxy-2-chloro-pyrimidine (880 mg, 3.99 mmol), cuprous iodide (158 mg, 0.830 mmol), N,N'-bis(2-phenoxyphenyl)oxamide (220 mg, 0.804 mmol) and potassium phosphate tribasic (2.612 g, 12.06 mmol) with DMF (10 mL). Stir the resultant mixture under N$_2$ and heat to 100° C. for 6 hrs. Dilute the mixture with EtOAc and filter through diatomaceous earth.

Concentrate the filtrate and subject the resulting crude material to silica gel flash chromatography eluting with 7% MeOH in DCM to give the title compound (869 mg, 61%) as a yellow solid. LCMS (m/z): 353.2 [M+H]$^+$ Preparation 20

8-(5-Benzyloxypyrimidin-2-yl)-2-methyl-2,8-diazaspiro[4.5]decan-1-one

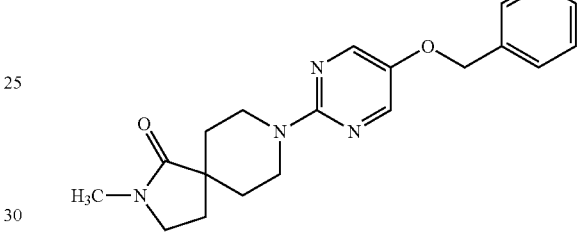

Add sodium hydride in mineral oil (60 mass %, 66 mg, 1.6 mmol) to a solution of 8-(5-benzyloxypyrimidin-2-yl)-2,8-diazaspiro[4.5]decan-1-one (0.39 g, 1.1 mmol) in DMF (8.0 mL); stir the mixture at 0° C. for 20 min. Add iodomethane (0.31 g, 2.2 mmol) to the cold (0° C.) mixture. Allow the mixture to warm to ambient temperature and stir the mixture for 1 hr. Quench the reaction with water (30 mL). Extract the resulting mixture with EtOAc (2×15 mL). Combine the organic extracts and wash with brine (2×20 mL); dry over anhydrous Na$_2$SO$_4$; filter; and concentrate the filtrate under vacuum to give the title compound (0.42 g, 98%) as a yellow solid, which can be used without further purification. $^1$H NMR (400 MHz, CDCl$_3$) δ 8.04 (s, 2H), 7.38-7.24 (m, 5H), 4.95 (s, 2H), 4.42 (dt, J=4.0, 13.6 Hz, 2H), 3.27 (t, J=6.8 Hz, 2H), 3.15-3.02 (m, 2H), 2.79 (s, 3H), 1.96 (t, J=6.8 Hz, 2H), 1.90-1.78 (m, 2H), 1.42-1.34 (m, 2H).

Alternate Preparation 20

8-(5-Benzyloxypyrimidin-2-yl)-2-methyl-2,8-diazaspiro[4.5]decan-1-one

Combine 5-benzyloxy-2-chloro-pyrimidine (24.824 g, 112.50 mmol), 2-methyl-2,8-diazaspiro[4.5]decan-1-one hydrochloride (29.736 g, 145.27 mmol) and potassium carbonate (46.643 g, 337.50 mmol) in NMP. Add NMP (170 mL) and triethylamine (23.5 mL, 168.75 mmol) and heat the mixture to 130° C. for 30 hrs. Cool the mixture, filter to collect the solid, then wash the solid with EtOAc. Concentrate the filtrate and pour the concentrated solution into crushed ice (about 1.2 L). A light brown solid precipitates immediately. Stir the mixture for 30 min and then allow the mixture to stand at room temperature overnight. Filter the mixture to collect the solid and wash the solid with MTBE (400 mL). Dry the solid under vacuum at 50° C. for 1.5 days to give the title compound (36.924 g, 88.48%) as a pale brown solid, which can be used without further purification. ES/MS (m/z) 353.3 (M+H).

Preparation 21

8-(5-Benzyloxypyrimidin-2-yl)-2-(cyclopropylmethyl)-2,8-diazaspiro[4.5]decan-1-one

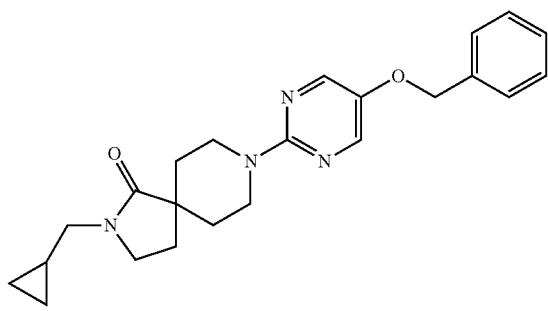 [SMILES: O=C1N(CC2CC2)CCC12CCN(c1ncc(OCc3ccccc3)cn1)CC2]

Add sodium hydride in mineral oil (22 mg, 0.55 mmol, 60 mass %) to a stirred solution of 8-(5-benzyloxypyrimidin-2-yl)-2,8-diazaspiro[4.5]decan-1-one (60 mg, 0.18 mmol) in DMF (5.0 mL) at 0° C. Allow the mixture to warm to room temperature and stir for 5 min. Add (bromomethyl)cyclopropane (100 mg, 0.71 mmol) and stir the resulting mixture at room temperature for 16 hrs. Evaporate the solvent under reduced pressure to give the crude product. Subject the material to silica gel flash chromatography eluting with 40% EtOAc in hexanes to give the title product (40 mg, 55%) as a white solid. LCMS (m/z): 392.2 [M+H]

Preparation 22

9-(5-Benzyloxypyrimidin-2-yl)-2-methyl-2,9-diazaspiro[5.5]undecan-1-one

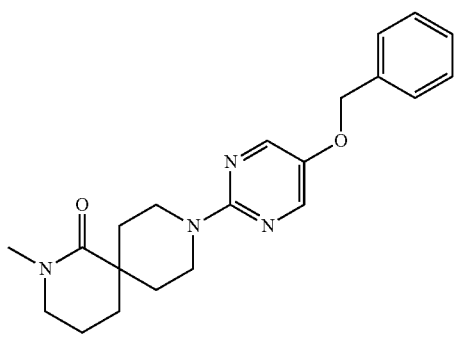 [SMILES: CN1CCCC2(CCN(c3ncc(OCc4ccccc4)cn3)CC2)C1=O]

Dissolve 9-(5-benzyloxypyrimidin-2-yl)-2,9-diazaspiro[5.5]undecan-1-one (183 mg, 0.51 mmol) in THF (8 mL) and cool the solution to 0° C. Add sodium hydride (41 mg, 1.018 mmol, 60 mass %) in one portion. Stir the solution at 0° for 15 min. Add iodomethane (0.064 mL, 1.02 mmol) at 0°, warm the mixture to room temperature and stir for 30 min. Cool the mixture to 0° add further sodium hydride (20 mg, 0.51 mmol) and stir for 15 min. Add iodomethane (0.032 mL, 0.51 mmol), warm the mixture to room temperature, and stir for 30 min. Add saturated NH₄Cl (aq) to quench the reaction and dilute with EtOAc. Separate the organic phase and extract the aqueous phase with EtOAc (2×). Combine the organic extracts, dry over Na₂SO₄, filter, concentrate the filtrate to provide a residue. Subject the residue to silica gel flash chromatography eluting with 75% EtOAc in hexanes to give the title compound (158 mg, 83%). LCMS (m/z): 367.2 [M+H]⁺

Preparation 23

8-(5-Hydroxypyrimidin-2-yl)-2-methyl-2,8-diazaspiro[4.5]decan-1-one

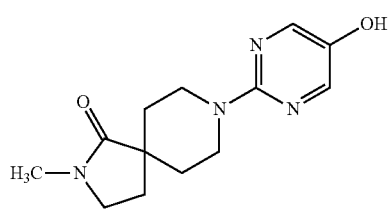 [SMILES: CN1CCC2(CCN(c3ncc(O)cn3)CC2)C1=O]

Add palladium on carbon (50% in water, 10% w, 42 mg) to a solution of 8-(5-benzyloxypyrimidin-2-yl)-2-methyl-2,8-diazaspiro[4.5]decan-1-one (0.42 g, 1.1 mmol) in MeOH (40 mL). Stir the mixture at room temperature under a hydrogen atmosphere for 4 hrs and then at 40° C. for 6 hrs. Filter the mixture through a pad of diatomaceous earth. Concentrate the filtrate under vacuum to give the title compound (0.34 g, 97%) as a light yellow solid, which can be used without further purification. ¹H NMR (400 MHz, CDCl₃) δ 8.05 (s, 2H), 4.54-4.44 (m, 2H), 3.37 (t, J=7.2 Hz, 2H), 3.15-3.05 (m, 2H), 2.88 (s, 3H), 2.07 (t, J 7.2 Hz, 2H), 1.96-1.88 (m, 2H), 1.45-1.40 (m, 2H), ES/MS (m/z) 262.9 (M+H).

Alternate Preparation 23

8-(5-Hydroxypyrimidin-2-yl)-2-methyl-2,8-diazaspiro[4.5]decan-1-one

Transfer a suspension of 8-(5-benzyloxypyrimidin-2-yl)-2-methyl-2,8-diazaspiro[4.5]decan-1-one (18.190 g, 49.04 mmol) in EtOAc (100 mL) and MeOH (100 mL) to a high pressure reactor, to which is added a suspension of 5% palladium on activated carbon (1.84 g, 0.865 mmol) in MeOH (40 mL). Hydrogenate the mixture under 310 kPa hydrogen for 4 hrs in a Parr™ shaker. Dilute the mixture with MeOH and filter the mixture through diatomaceous earth. Concentrate the filtrate to dryness to give the title compound (12.9 g, 46.7 mmol, 95.3%) as yellow solid which is used without further purification. ES/MS (m/z) 263.3 (M+H).

Preparation 24

2-Cyclopropyl-8-(5-hydroxypyrimidin-2-yl)-2,8-diazaspiro[4.5]decan-1-one

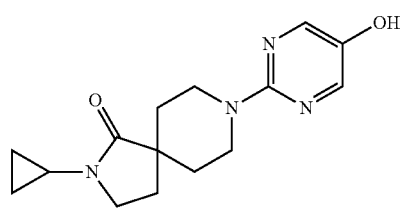 [SMILES: O=C1N(C2CC2)CCC12CCN(c1ncc(O)cn1)CC2]

Dissolve 8-(5-benzyloxypyrimidin-2-yl)-2-cyclopropyl-2,8-diazaspiro[4.5]decan-1-one (39 mg, 0.10 mmol) in EtOAc (2.0 mL). Suspend palladium on active carbon (10 mg, 0.005 mmol, 5 mass %) in MeOH (1.0 mL) and transfer to the above solution. Add 1,4-cyclohexadiene (0.096 mL, 1.01 mmol) and stir the resultant mixture at room temperature overnight. Dilute the mixture with EtOAc and filter through diatomaceous earth. Concentrate the filtrate to give the title compound (29 mg, 98%) as white solid, which is directly used without further purification. LCMS (m/z): 289.1 [M+H]$^+$ Preparation 25

2-(Cyclopropylmethyl)-8-(5-hydroxypyrimidin-2-yl)-2,8-diazaspiro[4.5]decan-1-one

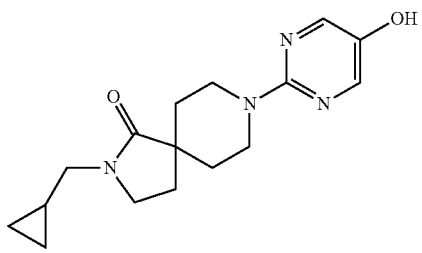 [SMILES: O=C1N(CC2CC2)CCC12CCN(c1ncc(O)cn1)CC2]

Stir together 8-(5-benzyloxypyrimidin-2-yl)-2-(cyclopropylmethyl)-2,8-diazaspiro[4.5]decan-1-one (40 mg, 0.097 mmol) and palladium on carbon (20 mg, 5 mass %) in MeOH (10 mL) under a H$_2$ atmosphere at room temperature for 16 hrs. Filter the mixture through diatomaceous earth and concentrate the filtrate under reduced pressure to give the crude product, which is subjected to silica gel flash chromatography eluting with 80% EtOAc and 20% hexanes to give the title compound (17 mg, 55%) as a white solid. LCMS (m/z): 303.3 [M+H]

Preparation 26

9-(5-Hydroxypyrimidin-2-yl)-2,9-diazaspiro[5.5]undecan-1-one

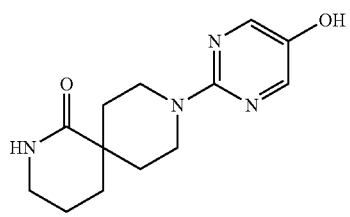 [SMILES: O=C1NCCCC12CCN(c1ncc(O)cn1)CC2]

Suspend palladium on active carbon (50 mg, 0.023 mmol) in MeOH (15 mL) and add to 9-(5-benzyloxypyrimidin-2-yl)-2,9-diazaspiro[5.5]undecan-1-one (97 mg, 0.27 mmol). Equip with a hydrogen balloon, evacuate with hydrogen 3 times, and stir the resultant mixture at room temperature for 4 hrs. Dilute the mixture with MeOH and filter the solution through diatomaceous earth. Concentrate the filtrate to give the title compound (72 mg, 99%) as white solid, which is used directly without further purification. LCMS (m/z): 263.1 [M+H]$^+$ Prepare the following compounds essentially accordingly to the method of Preparation 26 and stir the mixture for 1-5 hrs.

| Prep No. | Chemical Name | Structure | ES/MS (m/z) [M + H]$^+$ |
|---|---|---|---|
| 27 | 9-(5-Hydroxypyrimidin-2-yl)-2-methyl-2,9-diazaspiro[5.5]undecan-1-one | 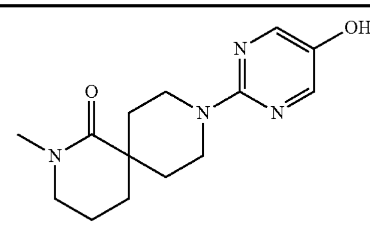 | 277.3 |
| 28 | 2-tert-Butyl-8-(5-hydroxypyrimidin-2-yl)-2,8-diazaspiro[4.5]decan-1-one | 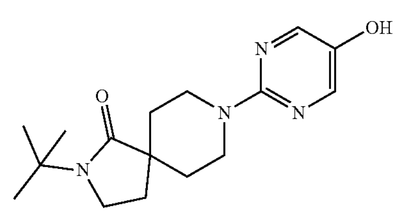 [SMILES: CC(C)(C)N1CCC2(CCN(c3ncc(O)cn3)CC2)C1=O] | 305.3 |
| 29 | 1-(5-Hydroxypyrimidin-2-yl)piperidine-4-carboxyamide | 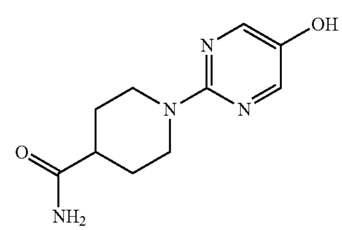 [SMILES: NC(=O)C1CCN(c2ncc(O)cn2)CC1] | 222.9 |

Preparation 30 tert-Butyl N-[(E)-3-fluoro-2-[[2-(2-methyl-1-oxo-2,8-diazaspiro[4.5]decan-8-yl)pyrimidin-5-yl]oxymethyl]allyl]carbamate

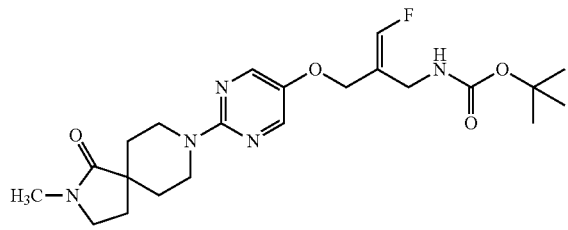 [SMILES: CN1CCC2(CCN(c3ncc(OC/C(=C/F)CNC(=O)OC(C)(C)C)cn3)CC2)C1=O]

Combine 8-(5-hydroxypyrimidin-2-yl)-2-methyl-2,8-diazaspiro[4.5]decan-1-one (0.14 g, 0.49 mmol), tert-butyl N-[(E)-2-(bromomethyl)-3-fluoro-allyl]carbamate (0.11 g, 0.41 mmol) and potassium carbonate (0.17 g, 1.2 mmol) in anhydrous DMF (5.0 mL). Warm the resulting mixture to 50° C. and stir for 1.5 hrs. Dilute the mixture with water (30 mL) and extract with EtOAc (2×15 mL). Combined the organic extracts; wash with brine (2×20 mL); dry over anhydrous Na$_2$SO$_4$; filter; and concentrate the filtrate under vacuum to provide a residue. Subject the residue to by flash chromatography on silica gel eluting with 0-0.5% MeOH in DCM to give the title compound (0.16 g, 82%) as a white solid. $^1$H NMR (400 MHz, CDCl$_3$) δ 8.09 (s, 2H), 6.70 (d, J 82.0 Hz, 2H), 4.78 (br s, 1H), 4.60-4.45 (m, 2H), 4.39 (s, 2H), 4.00 (s, 2H), 3.41-3.28 (m, 2H), 3.25-3.18 (m, 2H), 2.94-2.76 (m, 3H), 2.12-2.01 (m, 2H), 2.00-1.85 (m, 2H), 1.50-1.38 (m, 12H).

Alternate Preparation 30 tert-Butyl N-[(E)-3-fluoro-2-[[2-(2-methyl-1-oxo-2,8-diazaspiro[4.5]decan-8-yl)pyrimidin-5-yl]oxymethyl]allyl]carbamate Combine 8-(5-hydroxypyrimidin-2-yl)-2-methyl-2,8-diazaspiro[4.5]decan-1-one (12.9 g, 46.7 mmol), tert-butyl N-[(E)-2-(bromomethyl)-3-fluoro-allyl]carbamate (13.2 g, 49.1 mmol), and potassium carbonate (19.4 g, 140 mmol) with DMF (73 mL). Stir the resulting mixture at room temperature for 5 hrs. Dilute the mixture with EtOAc and filter through diatomaceous earth. Concentrate the filtrate to provide a residue. Subject the residue to silica gel flash chromatography eluting with 3% MeOH in DCM to give the title compound (18.6 g, 40.6 mmol, 86.8%) as yellow oil. ES/MS (m/z) 450.3 (M+H).

Prepare the following compounds essentially accordingly to the method of Alternate Preparation 30 and stir the reaction from 3 hrs to 64 hrs.

| Prep No. | Chemical Name | Structure | ES/MS (m/z) [M + H]$^+$ |
|---|---|---|---|
| 31 | tert-Butyl N-[(E)-3-fluoro-2-[[2-(2-methyl-1-oxo-2,9-diazaspiro[5.5]undecan-9-yl)pyrimidin-5-yl]oxymethyl]allyl]carbamate | 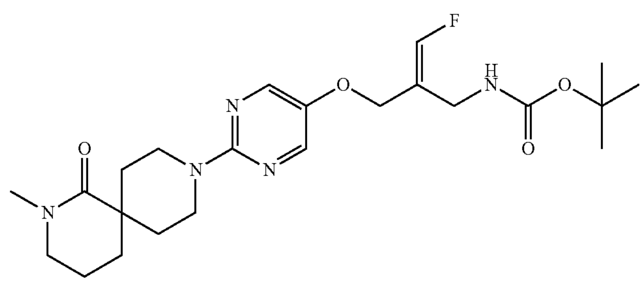 [SMILES: CN1CCCC2(CCN(c3ncc(OC/C(=C/F)CNC(=O)OC(C)(C)C)cn3)CC2)C1=O] | 464.3 |
| 32 | tert-Butyl N-[(E)-3-fluoro-2-[[2-(1-oxo-2,9-diazaspiro[5.5]undecan-9-yl)pyrimidin-5-yl]oxymethyl]allyl]carbamate | 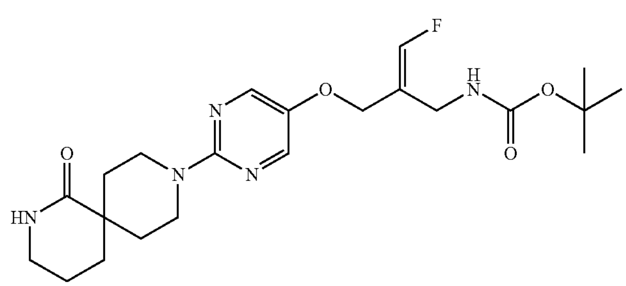 [SMILES: CC(C)(C)OC(=O)NC/C(=C\F)COc1cnc(N2CCC3(CCCNC3=O)CC2)nc1] | 450.2 |
| $^a$33 | tert-Butyl N-[(E)-2-[[2-(2-cyclopropyl-1-oxo-2,8-diazaspiro[4.5]decan-8-yl)pyrimidin-5-yl]oxymethyl]-3-fluoro-allyl]carbamate | | 476.2 |

| Prep No. | Chemical Name | Structure | ES/MS (m/z) [M + H]+ |
|---|---|---|---|
| 34 | tert-Butyl N-[(E)-2-[[2-[2-(cyclopropylmethyl)-1-oxo-2,8-diazaspiro[4,5]decan-8-yl]pyrimidin-5-yl]oxymethyl]-3-fluoro-allyl]carbamate | 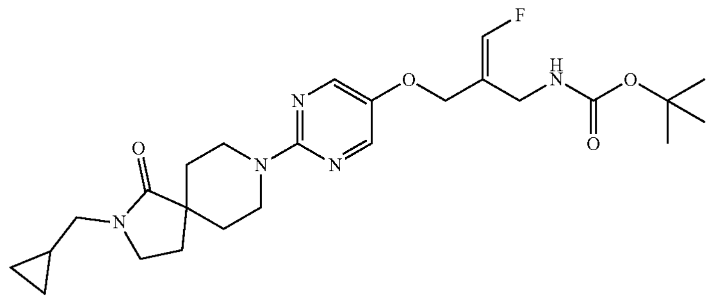 [SMILES: CC(C)(C)OC(=O)NC/C(=C\F)COc1cnc(N2CCC3(CCN(CC4CC4)C3=O)CC2)nc1] | 490.2 |
| 36 | tert-Butyl N-[(E)-2-[[2-(2-tert-butyl-1-oxo-2,8-diazaspiro[4.5]decan-8-yl)pyrimidin-5-yl]oxymethyl]-3-fluoro-allyl]carbamate | 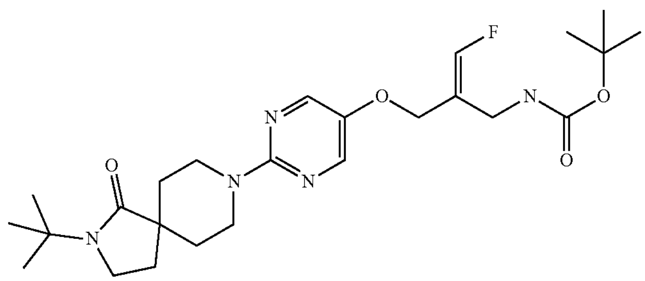 [SMILES: CC(C)(C)OC(=O)NC/C(=C\F)COc1cnc(N2CCC3(CC2)CCN(C(C)(C)C)C3=O)nc1] | 492.4 |

<sup>a</sup>Stir at room temperature and heat the reaction 80° C. for 1.5 hrs.

Preparation 37 tert-Butyl 4-[5-[(E)-2-[(tert-butoxycarbonylamino)methyl]-3-fluoro-allyloxy]-2-pyridyl]-2-oxo-piperazine-1-carboxylate

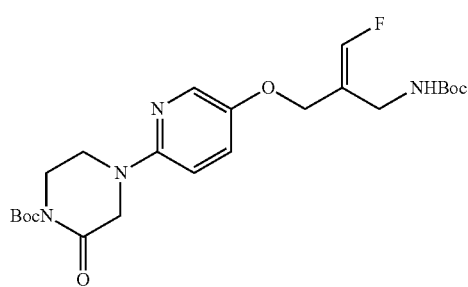 [SMILES: CC(C)(C)OC(=O)NC/C(=C\F)COc1ccc(N2CCN(C(=O)OC(C)(C)C)C(=O)C2)nc1]

Add tert-butyl N-[(E)-2-(bromomethyl)-3-fluoro-allyl]carbamate (0.12 g, 1.1 equiv., 0.450 mmol) and potassium carbonate (0.17 g, 3 equiv, 1.23 mmol) to a solution of tert-butyl 4-(5-hydroxy-2-pyridyl)-2-oxo-piperazine-1-carboxylate (120 mg, 0.409 mmol) in DMF (3 mL, 39 mmol). Stir the mixture at 70° C. for 2 hrs to give a yellow suspension. Add water (20 mL) to the mixture and extract the mixture with EtOAc (3×20 mL). Combine the extracts and wash the combined organic extracts with brine (2×20 mL). Concentrate the organic extracts to give the title compound (180 mg) as yellow oil, which is used directly without further purification. LCMS (ESI): m/s 381.2 [M+H]+.

Preparation 39 tert-Butyl N-[(E)-2-[[2-(4-carbamoyl-1-piperidyl)pyrimidin-5-yl]oxymethyl]-3-fluoro-allyl]carbamate

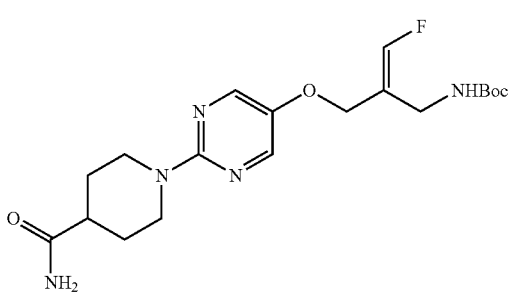 [SMILES: CC(C)(C)OC(=O)NC/C(=C\F)COc1cnc(N2CCC(C(N)=O)CC2)nc1]

Follow the procedure essentially accordingly to the method of Preparation 38, but use 2 equiv of potassium carbonate. ES/MS (m/z) [M+H]+ 410.2

Preparation 40 tert-Butyl N-[(E)-3-fluoro-2-[[2-(3-methyl-2-oxo-imidazolidin-1-yl)pyrimidin-5-yl]oxymethyl]allyl]carbamate

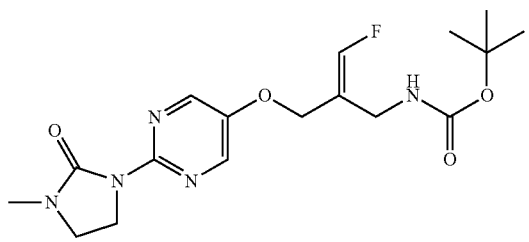 [SMILES: CN1CCN(c2ncc(OC/C(=C/F)CNC(=O)OC(C)(C)C)cn2)C1=O]

Heat a mixture of tert-butyl N-[(E)-2-[(2-chloropyrimidin-5-yl)oxymethyl]-3-fluoro-allyl]carbamate (114 mg, 0.36 mmol), methyl imidazolidinone (115 mg, 1.151 mmol), cuprous iodide (40.1 mg, 0.211 mmol), trans-N,N'-dimethylcyclohexane-1,2-diamine (40 μL), cesium carbonate (351 mg, 1.077 mmol), and 1,4-dioxane (10 mL) to 160° C. under microwave conditions for 3 hrs under N₂ atmosphere. Filter the reaction mixture and concentrate under vacuum. Subject the residue to a prep-HPLC with the following conditions: LC Column: SunFire C18 30×100 mm 5 μm; A: H₂O (0.1% FA); B: ACN (0.1% FA), gradient 24-39% ACN in 11 min, stop at 17 min; column temperature room temperature; flow rate 30 mL/min.; $t_{(R)}$=10.0 minutes (UV). Obtain the title product as a white solid. (137 mg, 27%). LCMS (ESI): m/s 382.2 [M+H]+.

Preparation 41 tert-Butyl N-[(E)-3-fluoro-2-[[2-(3-oxo-2,8-diazaspiro[4.5]decan-8-yl)pyrimidin-5-yl]oxymethyl]allyl]carbamate Stir a mixture of tert-butyl N-[(E)-2-[(2-chloropyrimidin-5-yl)oxymethyl]-3-fluoro-allyl]carbamate (65 mg, 0.20 mmol), 2,8-diazaspiro[4.5]decan-3-one (67 mg, 0.41 mmol), DIPEA(0.11 mL, 0.63 mmol) and 1,4-dioxane (5.0 mL) at 120° C. under microwave irradiation for 12 hrs. Evaporate the solvent under reduced pressure to give the crude product, which is subjected to silica gel flash chromatography eluting with a gradient of 0-5% MeOH in DCM to give the title compound (61 mg, 68.46%) as a white solid. LCMS (ESI): m/s 436.3 [M+H].

Prepare the following compounds essentially accordingly to the method of Preparation 41, heating from 110-120 OC from 3-12 hrs.

| Prep No. | Chemical Name | Structure | ES/MS (m/z) [M + H]+ |
|---|---|---|---|
| 42 | Methyl 1-[5-[(E)-2-[(tert-butoxycarbonylamino)methyl]-3-fluoro-allyloxy]pyrimidin-2-yl]piperidine-4-carboxylate | 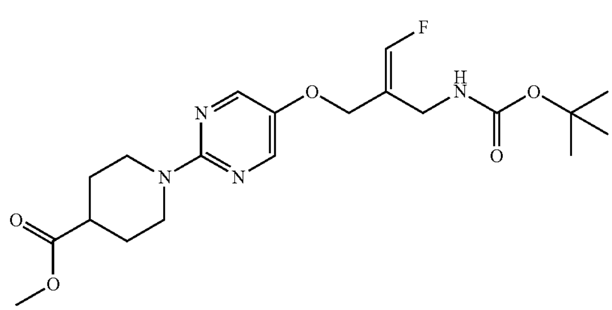 [SMILES: COC(=O)C1CCN(c2ncc(OC/C(=C/F)CNC(=O)OC(C)(C)C)cn2)CC1] | 425.3 |
| a43 | tert-Butyl N-[(E)-3-fluoro-2-[[2-[4-(2-oxopyrrolidin-1-yl)-1-piperidyl]pyrimidin-5-yl]oxymethyl]allyl]carbamate | | 45020 |

| Prep No. | Chemical Name | Structure | ES/MS (m/z) [M + H]+ |
|---|---|---|---|
| 44 | Ethyl 1-[5-[(E)-2-[(tert-butoxycarbonylamino)methyl]-3-fluoro-allyloxy]pyrimidin-2-yl]-4-methyl-piperidine-4-carboxylate | 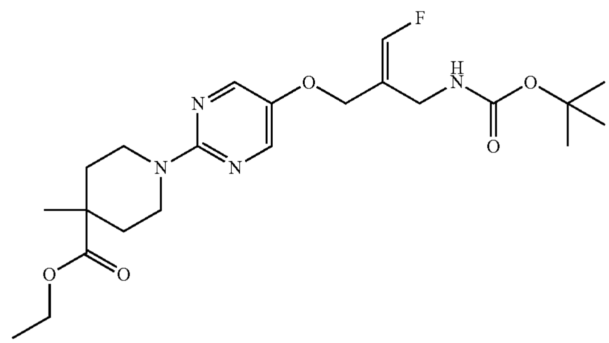 [SMILES: CCOC(=O)C1(C)CCN(c2ncc(OC/C(=C/F)CNC(=O)OC(C)(C)C)cn2)CC1] | 453.3 |
| a45 | tert-Butyl N-[(E)-2-[[2-[(3S)-3-(cyclopropylcarbamoyl)-1-piperidyl]pyrimidin-5-yl]oxymethyl]-3-fluoro-allyl]carbamate | | 450.4 |
| 46 | tert-Butyl N-[(E)-2-[[2-[(2-amino-2-methyl-propyl)amino]pyrimidin-5-yl]oxymethyl]-3-fluoro-allyl]carbamate | 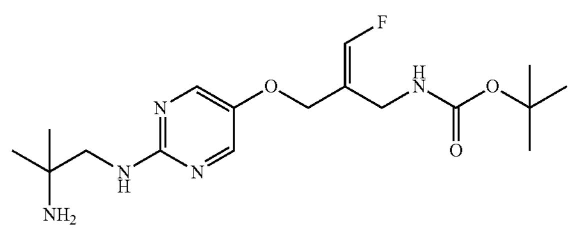 [SMILES: CC(C)(N)CNc1ncc(OC/C(=C/F)CNC(=O)OC(C)(C)C)cn1] | 370.2 |
| a47 | tert-Butyl N-[(E)-2-[[2-(3,3-dimethyl-5-oxo-piperazin-1-yl)pyrimidin-5-yl]oxymethyl]-3-fluoro-allyl]carbamate | | 410.3 |
| 48 | tert-Butyl N-[(E)-3-fluoro-2-[[2-(1-oxo-2,8-diazaspiro[4.5]decan-8-yl)pyrimidin-5-yl]oxymethyl]allyl]carbamate | 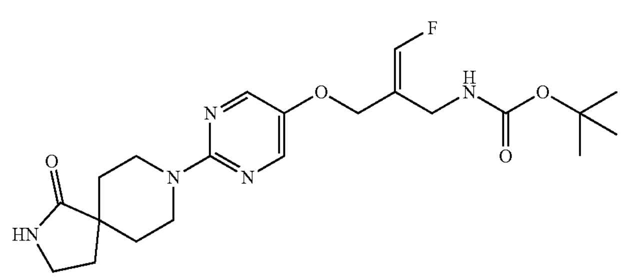 [SMILES: CC(C)(C)OC(=O)NC/C(=C\F)COc1cnc(N2CCC3(CCNC3=O)CC2)nc1] | 436.2 |

| Prep No. | Chemical Name | Structure | ES/MS (m/z) [M + H]+ |
|---|---|---|---|
| 49 | tert-Butyl N-[(E)-3-fluoro-2-[[2-[(1-oxo-2,9-diazaspiro[4.5]decan-9-yl)-pyrimidin-5-yl]oxymethyl]allyl]carbamate | 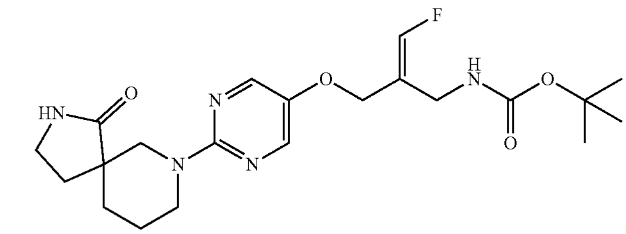 [SMILES: CC(C)(C)OC(=O)NC/C(=C\F)COc1cnc(N2CCCC3(CCNC3=O)C2)nc1] | 436.2 |
| 50 | tert-Butyl N-[(E)-3-fluoro-2-[[2-(3-oxo-2,7-diazaspiro[4.5]decan-7-yl)pyrimidin-5-yl]oxymethyl]allyl]carbamate | 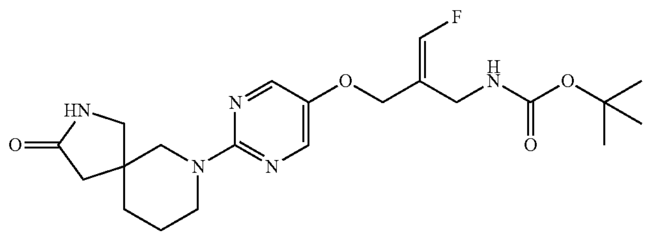 [SMILES: CC(C)(C)OC(=O)NC/C(=C\F)COc1cnc(N2CCCC3(CNC(=O)C3)C2)nc1] | 458.2 |

<sup>a</sup>See purification procedures below.

Purification of Preparation 43 tert-Butyl N-[(E)-3-fluoro-2-[[2-[4-(2-oxopyrrolidin-1-yl)-1-piperidyl]pyrimidin-5-yl]oxymethyl]allyl]carbamate Subject the crude material to prep-HPLC with the following conditions: Column: SunFire C18 30×100 mm 5 μm; A: H₂O (0.1% FA); B: ACN (0.1% FA), gradient: 33-48% ACN in 11 min, stop at 18 min; column temperature: room temperature; flow rate: 30 mL/min; t$_{(R)}$=8.7 minutes (UV) to provide the title compound (16 mg, 21%) as a white solid.

Purification of Preparation 45 tert-butyl N-[(E)-2-[[2-[(3 S)-3-(cyclopropylcarbamoyl)-1-piperidyl]pyrimidin-5-yl]oxymethyl]-3-fluoro-allyl]carbamate Subject the crude material to prep HPLC with the following conditions: Column: XBridge® C18 30×150 mm 5 μm; A: H₂O 10 mM NH₄HCO₃; B: ACN, gradient: 35-40% ACN in 11 min, stop at 17 min; column temperature: room temperature; flow rate: 35 mL/min; t$_{(R)}$=9.8 minutes (UV), to provide the title compound (120 mg, 53%).

Purification of Preparation 47 tert-Butyl N-[(E)-2-[[2-(3,3-dimethyl-5-oxo-piperazin-1-yl)pyrimidin-5-yl]oxymethyl]-3-fluoro-allyl]carbamate Subject the crude material to prep-HPLC with the following conditions: Column: SunFire C18 30×100 mm 5 μm; A: H₂O (0.1% FA); B: ACN (0.1% FA), gradient: 29-44% ACN in 11 min, stop at 17 min; column temperature: room temperature; flow rate: 30 mL/min; t$_{(R)}$=10.1 minutes (UV) to provide the title compound as a white solid (15 mg, 6%).

Preparation 51 tert-Butyl N-[(E)-2-[[2-(4,4-dimethyl-2-oxo-imidazolidin-1-yl)pyrimidin-5-yl]oxymethyl]-3-fluoro-allyl]carbamate

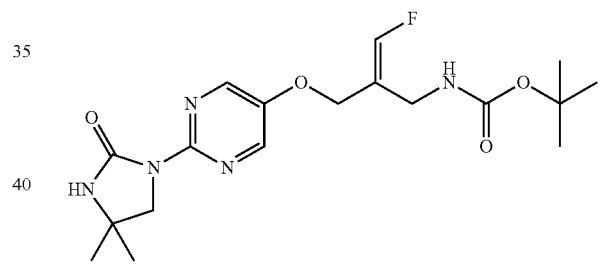

Dissolve tert-butyl N-[(E)-2-[[2-[(2-amino-2-methyl-propyl)amino]pyrimidin-5-yl]oxymethyl]-3-fluoro-allyl]carbamate (151 mg, 0.41 mmol) in THF (10 mL) and add 1,1'-carbonyldiimidazole (122 mg, 0.73 mmol) in one portion. Stir the mixture at room temperature overnight and then heat the mixture to 60° C. for 5 hrs. Concentrate the reaction mixture under vacuum use the crude mixture without further purification.

Preparation 52 tert-Butyl N-[(E)-3-fluoro-2-[[2-[4-(1-methyl-2-oxo-pyrrolidin-3-yl)oxy-1-piperidyl]pyrimidin-5-yl]oxymethyl]allyl]carbamate

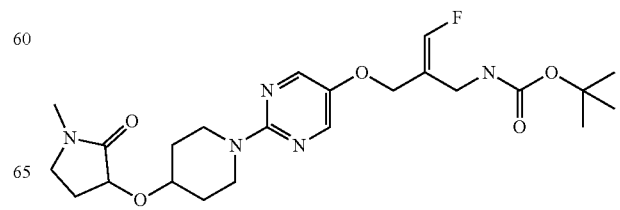

Stir a mixture of 1-methyl-3-(4-piperidyloxy)pyrrolidin-2-one (85 mg, 0.386 mmol), tert-butyl N-[(E)-2-[(2-chloropyrimidin-5-yl)oxymethyl]-3-fluoro-allyl]carbamate (0.123 g, 0.386 mmol) and DIPEA (0.102 g, 0.772 mmol, 0.135 mL) in NMP (2.0 mL) at 100° C. for 16 hrs. Dilute the reaction mixture with water (30 mL) and extract the mixture with EtOAc (3×15 mL). Wash the combined organic extracts with brine (3×30 mL), dry over anhydrous $Na_2SO_4$, filter, and concentrate the filtrate under vacuum. Subject the residue to silica gel flash chromatography eluting with 0-0.5% MeOH in DCM to give the title compound (85 mg, 41%) as a colorless gum. LCMS (m/z): 480.2 [M+H]$^+$, $^1$H NMR (400 MHz, CDCl$_3$) δ 8.08 (s, 2H), 6.70 (d, J=81.6 Hz, 1H), 4.77 (br s, 1H), 4.39 (d, J=3.6 Hz, 2H), 4.38-4.25 (m, 2H), 4.20-4.14 (m, 1H), 4.13-4.05 (m, 1H), 4.04-3.94 (m, 2H), 3.45-3.36 (m, 1H), 3.35-3.20 (m, 3H), 2.87 (s, 3H), 2.42-2.28 (m, 1H), 2.06-1.94 (m, 3H), 1.62-1.50 (m, 2H), 1.43 (s, 9H)

Preparation 53

1-[5-[(E)-2-[(tert-Butoxycarbonylamino)methyl]-3-fluoro-allyloxy]pyrimidin-2-yl]piperidine-4-carboxylic Acid

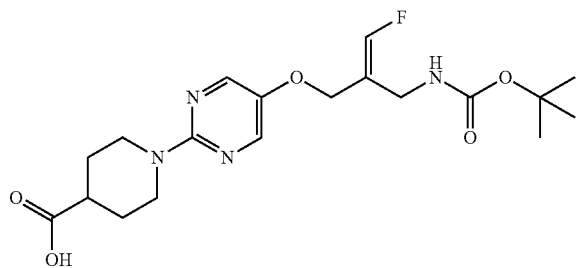 [SMILES: CC(C)(C)OC(=O)NC/C(=C\F)COc1cnc(N2CCC(C(=O)O)CC2)nc1]

Add lithium hydroxide (300 mg, 12.5 mmol) to a stirred solution of methyl 1-[5-[(E)-2-[(tert-butoxycarbonylamino)methyl]-3-fluoro-allyloxy]pyrimidin-2-yl]piperidine-4-carboxylate (260 mg, 0.55 mmol) in a mixture of THF (8.0 mL) and water (4.0 mL). Stir the resulting mixture at room temperature for 16 hrs. Filter to remove the solid and concentrate the filtrate to give the crude title product, which can be used directly without further purification. LCMS (ESI): m/s 411.3[M+H].

Preparation 54

1-[5-[(E)-2-[(tert-butoxycarbonylamino)methyl]-3-fluoro-allyloxy]pyrimidin-2-yl]-4-methyl-piperidine-4-carboxylic Acid

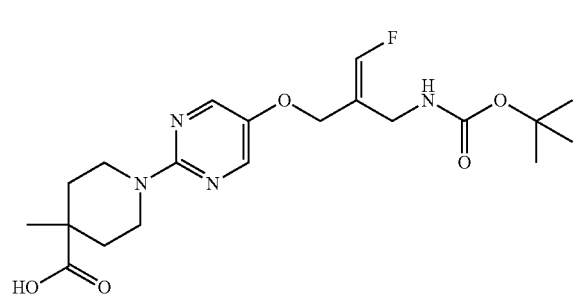 [SMILES: CC(C)(C)OC(=O)NC/C(=C\F)COc1cnc(N2CCC(C)(C(=O)O)CC2)nc1]

Add lithium hydroxide (19 mg, 0.79 mmol) to a stirred solution of ethyl 1-[5-[(E)-2-[(tert-butoxycarbonylamino)methyl]-3-fluoro-allyloxy]pyrimidin-2-yl]-4-methyl-piperidine-4-carboxylate (35 mg, 0.077 mmol) in a mixture of THF (4.0 mL) and water (2.0 mL). Stir the resulting mixture at room temperature for 16 hrs. Then heat the mixture to 100° C. under microwave irradiation for 2 hrs. Add 10% HCl to adjust the pH to about 3 and evaporate the mixture to dryness under reduced pressure to give the crude title product as a white solid, which is used directly without further purification. LCMS (ESI): m/s 425.3[M+H].

Preparation 55 tert-Butyl N-[(E)-2-[[2-[4-(dimethylcarbamoyl)-1-piperidyl]pyrimidin-5-yl]oxymethyl]-3-fluoro-allyl]carbamate

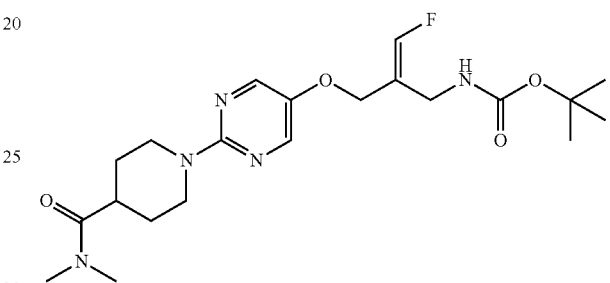

Add dimethylamine in THF (0.10 mL, 0.20 mmol, 2 mol/L) to a stirred solution of 1-[5-[(E)-2-[(tert-butoxycarbonylamino)methyl]-3-fluoro-allyloxy]pyrimidin-2-yl]piperidine-4-carboxylic acid (60 mg, 0.14 mmol) in DMF (4.0 mL), followed by the addition of HATU (0.10 g, 0.26 mmol) and DIPEA(0.05 mL, 0.3 mmol). Stir the mixture at room temperature for 16 hrs. Remove the solvent under reduced pressure to give the crude product, which is purified by prep-HPLC using the following conditions: Column: SunFire C18 30×100 mm 5 μm; A: $H_2O$ (0.1% FA); B: ACN (0.1% FA), gradient: 31-46% ACN in 11 min, stop at 18 min; column temperature: room temperature; flow rate: 30 mL/min; t$_{(R)}$=9.2 minutes (UV). Isolate the title product (23 mg, 37%) as a white solid. LCMS (ESI): m/s 438.4[M+H].

Preparation 56 tert-Butyl N-[(E)-3-fluoro-2-[[2-[4-[(3 S)-3-hydroxypyrrolidine-1-carbonyl]-1-piperidyl]pyrimidin-5-yl]oxymethyl]allyl]carbamate

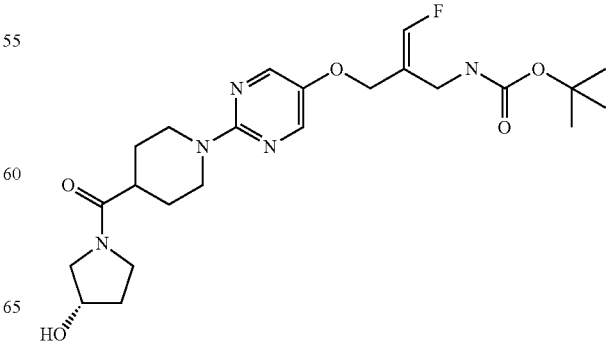

Follow the procedure essentially accordingly to the method of Preparation 55 using the appropriate amine, pyrrolidin-3-ol.

Example 1

8-[5-[(E)-2-(Aminomethyl)-3-fluoro-allyloxy]pyrimidin-2-yl]-2-methyl-2,8-diazaspiro[4.5]decan-1-one Dihydrochloride

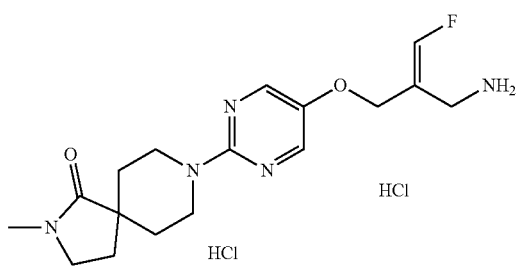 [SMILES: CN1CCC2(CCN(c3ncc(OC/C(=C/F)CN)cn3)CC2)C1=O ; Cl ; Cl]

Dissolve tert-butyl N-[(E)-3-fluoro-2-[[2-(2-methyl-1-oxo-2,8-diazaspiro[4.5]decan-8-yl)pyrimidin-5-yl]oxymethyl]allyl]carbamate (0.16 g, 0.34 mmol) in 3 M HCl in MeOH (5.0 mL). Stir the resulting mixture at room temperature for 1 hr. Concentrate the mixture under vacuum to give a residue. Dissolve the residue in water (5 mL); lyophilize the mixture to give the title compound (0.13 g, 86%) as a light yellow gum. ES/MS (m/z) 350.2 (M+H).

Example 2

8-[5-[(E)-2-(Aminomethyl)-3-fluoro-allyloxy]pyrimidin-2-yl]-2-methyl-2,8-diazaspiro[4.5]decan-1-one

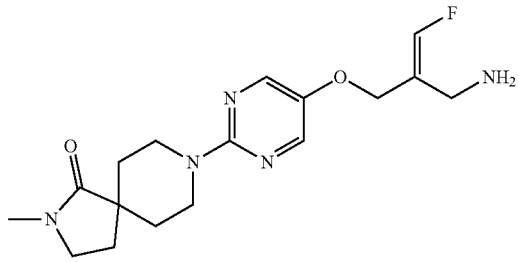 [SMILES: CN1CCC2(CCN(c3ncc(OC/C(=C/F)CN)cn3)CC2)C1=O]

Add a saturated, aqueous solution of potassium carbonate (100 mL) and 2-methyl-THF (200 mL) to 8-[5-[(E)-2-(aminomethyl)-3-fluoro-allyloxy]pyrimidin-2-yl]-2-methyl-2,8-diazaspiro[4.5]decan-1-one dihydrochloride (9.17 g, 21.2 mmol). Separate the aqueous layer from the organic layer. Wash the aqueous layer with 2-methyl-THF (200 mL) and add the organic extracts to the organic layer. Dry the organic layer over NaSO$_4$; filter; and concentrate the filtrate under vacuum to give the title compound (85 mass %, 7.47 g, 18.2 mmol, 85.9%). ES/MS (m/z) 350.2 (M+H).

Example 3

4-[5-[(E)-2-(aminomethyl)-3-fluoro-allyloxy]-2-pyridyl]piperazin-2-one

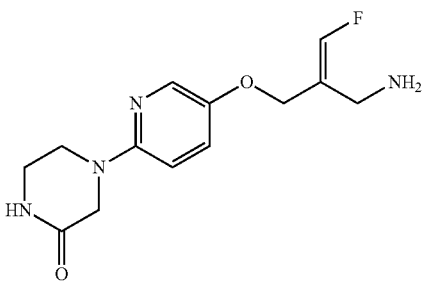 [SMILES: NC/C(=C\F)COc1ccc(N2CCNC(=O)C2)nc1]

Add HCl (3 mL, 4 M in 1,4-dioxane) to a solution of tert-butyl 4-[5-[(E)-2-[(tert-butoxycarbonylamino)methyl]-3-fluoro-allyloxy]-2-pyridyl]-2-oxo-piperazine-1-carboxylate (180 mg, 0.364 mmol) in 1,4-dioxane (2 mL). Stir the reaction mixture at room temperature for 2 hrs. Remove the solvent under reduced pressure to give the crude product as a yellow solid. Subject the material to prep-HPLC using the following conditions: Column: Kromasil C18 250*50 mm*10 μm, 1-30% B with A: water/0.05% NH$_4$OH, B: ACN, flow rate: 25 mL/min to give the title compound (20.2 mg, 19%). LCMS (ESI): m/s 280.9 [M+H]$^+$, $^1$H NMR (400 MHz, d$_4$-MeOH 7.95 (d, J=3.2 Hz, 1H), 7.37 (dd, J=9.2, 3.2 Hz, 1H), 6.97 (d, J=84 Hz, 1H), 6.83 (d, J=8.0 Hz, 1H), 4.57 (d, J=3.2 Hz, 2H), 4.03 (s, 2H), 3.71 (t, 0.1=4.0 Hz, 2H), 3.62-3.55 (m, 2H), 3.44 (t, J=4.0 Hz, 2H).

Example 4

3-[[1-[5-[(E)-2-(Aminomethyl)-3-fluoro-allyloxy]pyrimidin-2-yl]-4-piperidyl]oxy]-1-methyl-pyrrolidin-2-one Dihydrochloride

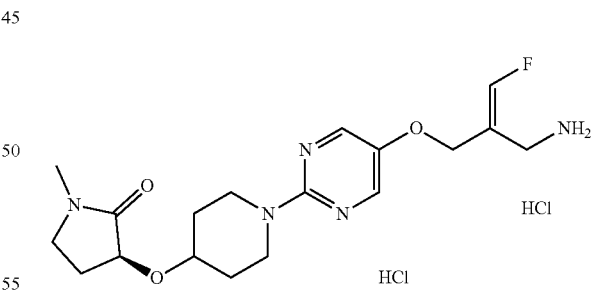

Stir a mixture of tert-butyl N-[(E)-3-fluoro-2-[[2-[4-(1-methyl-2-oxo-pyrrolidin-3-yl)oxy-1-piperidyl]pyrimidin-5-yl]oxymethyl]allyl]carbamate (85 mg, 0.160 mmol) in HCl in MeOH (4.0 mL, 4 M at room temperature for 1 hr and then concentrate the reaction mixture under vacuum. Subject the residue to prep-HPLC using the following conditions: Column:YMC-Actus Triart C18 150*30 mm*5 μm, 0-30% B with A: water/0.05% HCl, B: ACN, flow rate: 25 mL/min to give the title compound (45 mg, 61%) as a yellow gum. LCMS (m/z): 380.3 [M+H]$^+$, $^1$H NMR (400 MHz, d$_4$-MeOH) δ 6.86 (s, 2H), 5.68 (d, J=80.4 Hz, 1H), 3.13 (d, J=2.8 Hz, 2H), 2.73 (t, J=7.8 Hz, 1H), 2.55-2.41 (m, 3H), 2.29-2.14 (m, 4H), 1.88-1.76 (m, 2H), 1.29 (s, 3H), 0.95-0.81 (m, 1H), 0.52-0.15 (m, 5H)

Example 5

1-[5-[(E)-2-(Aminomethyl)-3-fluoro-allyloxy]pyrimidin-2-yl]-3-methyl-imidazolidin-2-one Hydrochloride

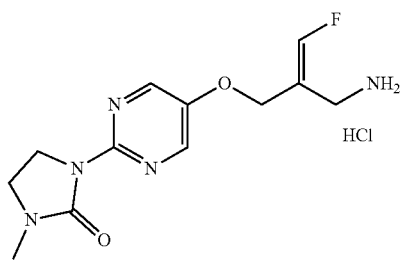 [SMILES: CN1CCN(c2ncc(OC/C(=C/F)CN)cn2)C1=O ; Cl]

Dissolve tert-butyl N-[(E)-3-fluoro-2-[[2-(3-methyl-2-oxo-imidazolidin-1-yl)pyrimidin-5-yl]oxymethyl]allyl]carbamate (35.1 mg, 0.0920 mmol) in HCl (10 mL, 1 M in EtOAc) and stir the resulting solution overnight. Concentrate the suspension under vacuum, dissolve in water and lyophilize the solution to give the title compound as an off-white solid. (24 mg, 63%). LCMS (ESI): m/s 282.2 [M+H]$^+$.

Prepare the following compounds essentially analogous to the method of Example 5 using the appropriately BOC protected allylmethylamine.

Example 8

1-[5-[(E)-2-(Aminomethyl)-3-fluoro-allyloxy]pyrimidin-2-yl]piperidine-4-carboxamide Hydrochloride

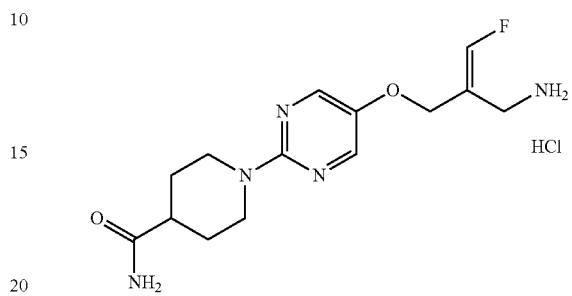

Stir a mixture of tert-butyl N-[(E)-2-[[2-(4-carbamoyl-1-piperidyl)pyrimidin-5-yl]oxymethyl]-3-fluoro-allyl]carbamate (80.0 mg, 0.195 mmol) in HCl (8 mL, 4 M in MeOH) at 10° C. for 2 hrs. Concentrate the reaction mixture under reduced pressure.

Purify the residue prep-HPLC eluting with 0.05% HCl to give the title compound (43.0 mg, 62%) as a yellow solid. LCMS (ESI): m/s 309.9 [M+H], $^1$H NMR (400 MHz, d$_4$-MeOH) δ 8.49 (s, 2H), 7.28 (d, J=80.4 Hz, 1H), 4.74 (d, J=2.8 Hz, 2H), 4.60-4.47 (m, 2H), 3.86 (s, 2H), 3.41-3.33 (m, 2H), 2.78-2.60 (m, 1H), 2.08-1.95 (m, 2H), 1.87-1.72 (m, 2H).

| Ex No. | Chemical Name | Structure | ES/MS (m/z) [M + H]$^+$ |
|---|---|---|---|
| $^a$6 | 4-[5-[(E)-2-(aminomethyl)-3-fluoro-allyloxy]pyrimidin-2-yl]-6,6-dimethyl-piperazin-2-one; dihydrochloride | 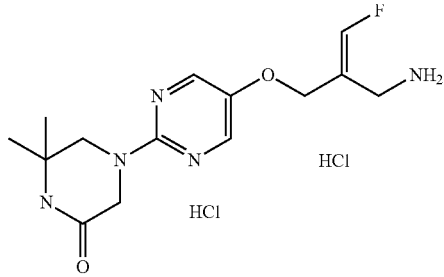 [SMILES: CC1(C)CN(c2ncc(OC/C(=C/F)CN)cn2)CC(=O)N1 ; Cl ; Cl] | 310.3 |
| $^b$7 | 1-[5-[(E)-2-(aminomethyl)-3-fluoro-allyloxy]pyrimidin-2-yl]-4,4-dimethyl-imidazolidin-2-one | 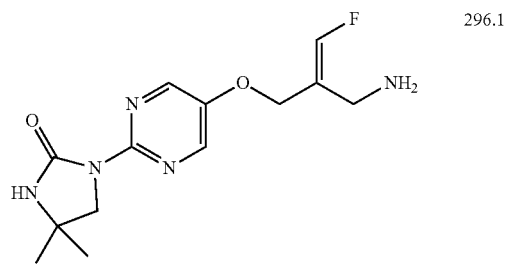 | 296.1 |

$^a$pre-mix with 1 mL 0.5 mol/L HCl in MeOH
$^b$Heat the mixture to 80° C. for 1 hr.

Example 9

8-[5-[(E)-2-(Aminomethyl)-3-fluoro-allyloxy]pyrimidin-2-yl]-2,8-diazaspiro[4.5]decan-3-one Dihydrochloride

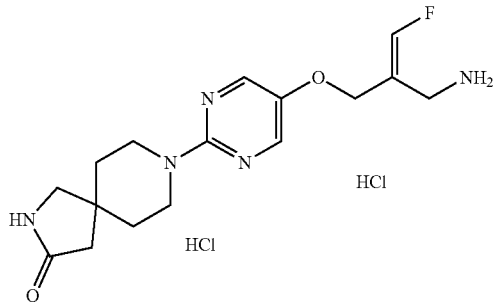 [SMILES: NC/C(=C\F)COc1cnc(N2CCC3(CC2)CNC(=O)C3)nc1 ; Cl ; Cl]

Stir a mixture of tert-butyl N-[(E)-3-fluoro-2-[[2-(3-oxo-2,8-diazaspiro[4.5]decan-8-yl)pyrimidin-5-yl]oxymethyl]allyl]carbamate (61 mg, 0.1401 mmol, 100 mass %) and HCl in MeOH (4.0 mL, 0.39 mol/L) at 60° C. under microwave irradiation for 2 hrs. Evaporate the solvent under reduced pressure to give the title compound as a yellow solid (60 mg, 99%). LCMS (ESI): m/s 336.3 [M+H].

Prepare the following compounds essentially analogous to the method of Example 9, heating the reaction to between about 60-80° C. for 5 min-2 hrs.

| Ex No. | Chemical Name | Structure | ES/MS (m/z) [M + H]+ |
|---|---|---|---|
| 10 | 8-[5-[(E)-2-(Aminomethyl)-3-fluoro-allyloxy]pyrimidin-2-yl]-2,8-diazaspiro[4.5]decan-1-one dihydrochloride | 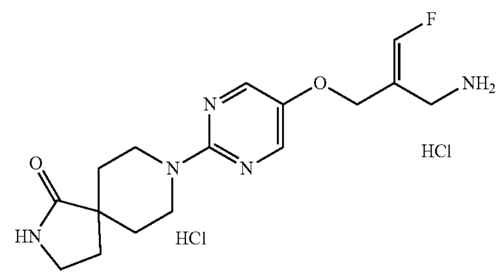 [SMILES: NC/C(=C\F)COc1cnc(N2CCC3(CCNC3=O)CC2)nc1 ; Cl ; Cl] | 336.2 |
| 11 | 9-[5-[(E)-2-(Aminomethyl)-3-fluoro-allyloxy]pyrimidin-2-yl]-2,9-diazaspiro[4.5]decan-1-one dihydrochloride | 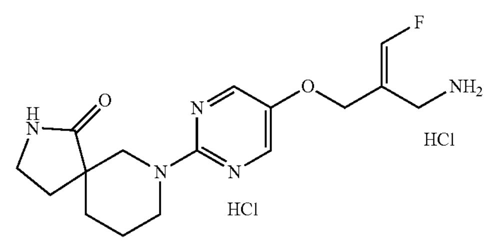 [SMILES: NC/C(=C\F)COc1cnc(N2CCCC3(CCNC3=O)C2)nc1 ; Cl ; Cl] | 336.2 |
| 12 | 7-[5-[(E)-2-(Aminomethyl)-3-fluoro-allyloxy]pyrimidin-2-yl]-2,7-diazaspiro[4.5]decan-3-one | 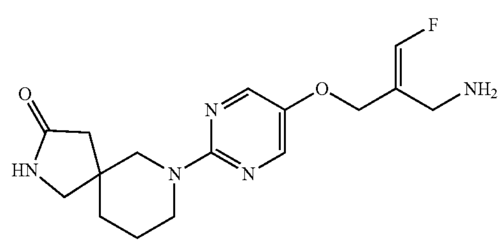 [SMILES: NC/C(=C\F)COc1cnc(N2CCCC3(CNC(=O)C3)C2)nc1] | 336.2 |
| 13 | (3S)-1-[5-[(E)-2-(Aminomethyl)-3-fluoro-allyloxy]pyrimidin-2-yl]-N-cyclopropyl-piperidine-3-carboxyamide hydrochloride | 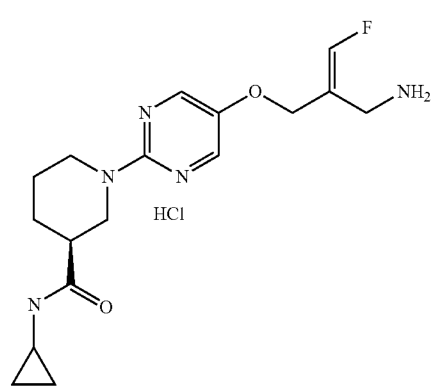 [SMILES: NC/C(=C\F)COc1cnc(N2CCC[C@H](C(=O)NC3CC3)C2)nc1 ; Cl] | 350.4 |

-continued

| Ex No. | Chemical Name | Structure | ES/MS (m/z) [M + H]+ |
|---|---|---|---|
| 14 | 1-[1-[5-[(E)-2-(Aminomethyl)-3-fluoro-allyloxy]pyrimidin-2-yl]-4-piperidyl]pyrrolidin-2-one-dihydrochloride | 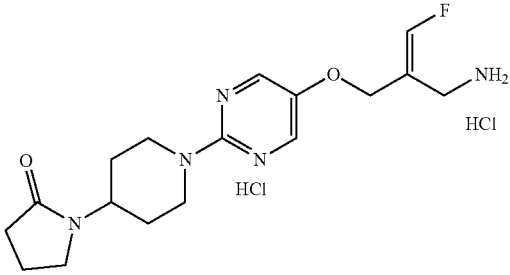 [SMILES: NC/C(=C\F)COc1cnc(N2CCC(N3CCCC3=O)CC2)nc1 ; Cl ; Cl] | 350.3 |
| 15 | 1-[5-[(E)-2-(Aminomethyl)-3-fluoro-allyloxy]pyrimidin-2-yl]-N,N-dimethyl-piperidine-4-carboxamide dihydrochloride | 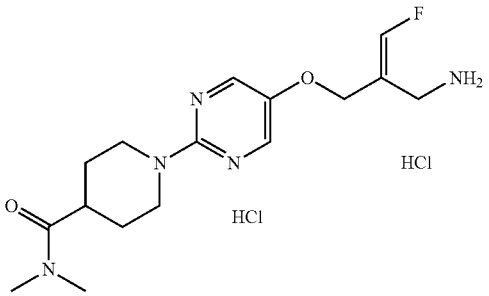 [SMILES: CN(C)C(=O)C1CCN(c2ncc(OC/C(=C/F)CN)cn2)CC1 ; Cl ; Cl] | 338.1 |
| 16 | [1-[5-[(E)-2-(Aminomethyl)-3-fluoro-allyloxy]pyrimidin-2-yl]-4-piperidyl]-[(3S)-3-hydroxypyrrolidin-1-yl]methanone dihydrochloride | 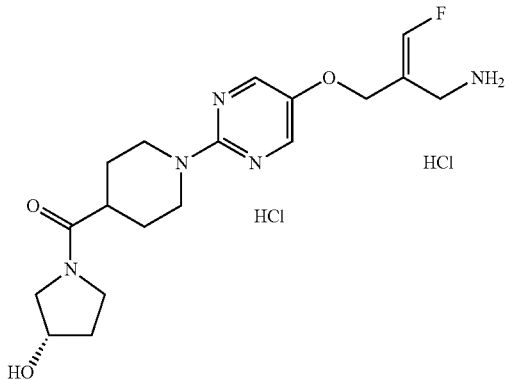 [SMILES: NC/C(=C\F)COc1cnc(N2CCC(C(=O)N3CC[C@H](O)C3)CC2)nc1 ; Cl ; Cl] | 380.3 |
| 17 | 8-[5-[(E)-2-(Aminomethyl)-3-fluoro-allyloxy]pyrimidin-2-yl]-2-(cyclopropylmethyl)-2,8-diazaspiro[4.5]decan-1-one dihydrochloride | 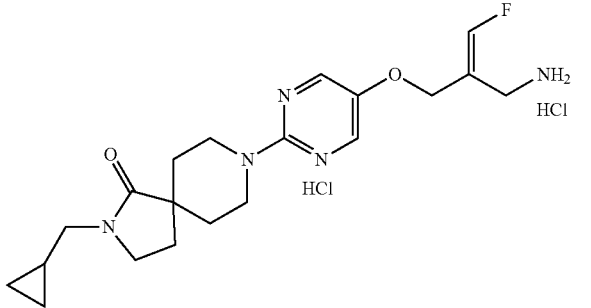 [SMILES: NC/C(=C\F)COc1cnc(N2CCC3(CCN(CC4CC4)C3=O)CC2)nc1 ; Cl ; Cl] | 390.2 |

| Ex No. | Chemical Name | Structure | ES/MS (m/z) [M + H]+ |
|---|---|---|---|
| a18 | 8-[5-[(E)-2-(Aminomethyl)-3-fluoro-allyloxy]pyrimidin-2-yl]-2-cyclopropyl-2,8-diazaspiro[4.5]decan-1-one dihydrochloride | | 376.2 |
| a19 | 9-[5-[(E)-2-(aminomethyl)-3-fluoro-allyloxy]pyrimidin-2-yl]-2,9-diazaspiro[5.5]undecan-1-one dihydrochloride | | 350.2 |
| b20 | 9-[5-[(E)-2-(Aminomethyl)-3-fluoro-allyloxy]pyrimidin-2-yl]-2-methyl-2,9-diazaspiro[5.5]undecan-1-one | | 364.2 |
| a21 | 8-[5-[(E)-2-(Aminomethyl)-3-fluoro-allyloxy]pyrimidin-2-yl]-2-tert-butyl-2,8-diazaspiro[4.5]decan-1-one dihydrochloride | | 392.4 |

[a] Dissolve the crude material in water and lyophilize to solid.
[b] See purification method below.

Purification of Example 12

7-[5-[(E)-2-(aminomethyl)-3-fluoro-allyloxy]pyrimidin-2-yl]-2,7-diazaspiro[4.5]decan-3-one Subject the crude material to prep-HPLC with the following conditions: LC column: XBridge® C18 30×150 mm 5 μm; A: H$_2$O 10 mM NH$_4$HCO$_3$; B: ACN, gradient: 0-5% ACN in 0-2 min, 10-20% ACN in 2-12 min, stop at 18 min; column temperature: room temperature; flow rate: 35 mL/min.; t$_{(R)}$=10.7 min. (UV) to provide the title product (8.5 mg, 36%) as a white solid.

Purification of Example 20

9-[5-[(E)-2-(Aminomethyl)-3-fluoro-allyloxy]pyrimidin-2-yl]-2-methyl-2,9-diazaspiro[5.5]undecan-1-one Dissolve the crude material in water and make basic with NaHCO$_3$. Subject the resulting material to prep-HPLC with the following conditions: LC Column: XBridge C18 30×100 mm 5 μm; A: H$_2$O (10 mM NH$_4$HCO$_3$); B: ACN, gradient: 10-25% B in 9 min, stop at 14 min; column temperature: room temperature; flow rate: 35 mL/min; t$_{(R)}$=8.7 min (UV) to provide the title compound (21 mg, 52%) as light yellow oil.

Example 22

1-[5-[(E)-2-(Aminomethyl)-3-fluoro-allyloxy]pyrimidin-2-yl]-N,N,4-trimethyl-piperidine-4-carboxamide Diformic Acid

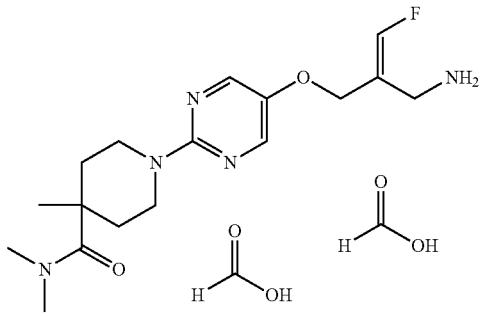 [SMILES: CN(C)C(=O)C1(C)CCN(c2ncc(OC/C(=C/F)CN)cn2)CC1 ; O=CO ; O=CO]

Add dimethylamine in THF (0.20 mL, 0.40 mmol, 2 mol/L) to a stirred solution of 1-[5-[(E)-2-[(tert-butoxycarbonylamino)methyl]-3-fluoro-allyloxy]pyrimidin-2-yl]-4-methyl-piperidine-4-carboxylic acid (32 mg, 0.075 mmol) in DMF (2.0 mL), followed by the addition of HATU (60 mg, 0.16 mmol) and DIPEA(0.065 mL, 0.37 mmol). Stir the mixture at room temperature for 16 hrs. Concentrate the mixture under reduced pressure to give the crude product. Subject the crude material to prep-HPLC using the following conditions: LC column: SunFire C18 30×100 mm 5 μm; A: H$_2$O (0.1% FA); B: ACN (0.1% FA), gradient: 5-5% ACN in 0-3 min, 5-10% ACN in 3-13 min, stop at 19 min; column temperature: room temperature; flow rate: 30 mL/min.; t$_{(R)}$=8.5 minutes (UV) to provide the title compound (15 mg, 43%) as a white solid. LCMS (ESI): m/s 352.2[M+H].

Biological Assays

SSAO/VAP-1 In Vitro Activity

Amine oxidase activity of recombinant hSSAO, hMAOa, and hMAOb isoforms are measured using the MAO-Glo™ assay kit from Promega (V1402). Test compounds (with DMSO as vehicle, 0.5% v/v for SSAO) and the enzyme are incubated for 10 mins at room temperature before the addition of the luminogenic substrate. The substrate concentration is 10 μM for human recombinant SSAO. The assays are conducted in a pH 7.4 buffer (50 mM HEPES, 120 mM NaCl, 5 mM KCl, 2 mM CaCl$_2$, 1.4 mM MgCl$_2$, 0.001% Tween-20) in a well-plate. Oxidation of the substrate is conducted for 2 hrs before the addition of detecting reagent according the manufacture's protocol. The IC$_{50}$ value of the tested compounds is calculated by fitting the dose response curve using a 4-parameter non-linear regression routine. The compounds of the Examples exhibit hSSAO inhibition IC$_{50}$ values of less than 100 nM. The IC$_{50}$ value for the compound of Example 1 is 19.36±5.68, n=5 (data is presented as mean±standard deviation).

The compounds of the Examples tested exhibited an IC$_{50}$ hMAOa and hMAOb more than 15 μM and 180 μM, respectively, indicating that the compounds of the Examples are selective for hSSAO over either hMAOa or hMAOb.

SSAO Target Engagement

The SSAO activity in rat plasma and liver tissues are measured using the MAO-Glo™ assay kit from Promega (V1402). The residual SSAO activity in rats after compound treatment is estimated by measuring the total amine oxidase activity in plasma or liver lysates that are insensitive to the presence of the MAO inhibitor Clogyline and Pargyline. Rats are administered the compound of Example 1 at the doses of 15, 3, 0.6, 0.12, 0.025, 0.005 mg/kg. The control group is administered with the same volume (2 ml/kg) of the dosing vehicle (hydroxyethyl cellulose 1% w/v, 0.25% Tween 80). Plasma and liver at 2 or 24 hrs post compound treatment are harvested and stored at −78° C. until analysis. Tissue lysates are prepared by homogenization in a lysis buffer (20 mM HEPES, pH 7.4, 150 mM NaCl, 1 mM EDTA, 1 mM EGTA, 1% Triton X-100 and 1× Roche Complete protease inhibitor tablet). Tissue particles are removed by centrifugation at 12,000 rpm at 4° C. for 30 min. 40 μl of plasma or liver lysates is incubated with Clogyline (10 μM) and Pargyline (10 μM) for 20 min. at room temperature before the addition of the luminogenic substrate (50 μM) for 60 min. The product generated is quantified according to the manufacture's procedure. The fraction of activity that is insensitive to the presence of the MAO inhibitors is used as the surrogate for the residual SSAO activity. The compound of Example 1 is evaluated in the protocol essentially as described above administered at various doses. The results are listed in the table below.

| | SSAO Target Engagement for Example 1 | | |
|---|---|---|---|
| | SSAO Activity (%) | | |
| Dose | Plasma | | Liver |
| (mg/kg) | 2 hours | 24 hours | 24 hours |
| Vehicle | | 100 ± 4 | 100 ± 18 |
| 0.005 | 76 ± 3 | 81 ± 4 | 79 ± 13 |
| 0.025 | 35 ± 4 | 67 ± 10 | 59 ± 14 |
| 0.12 | 17 ± 1 | 39 ± 4 | 28 ± 5 |
| 0.6 | 13.4 ± 2.4 | 31 ± 3 | 24 ± 6 |
| 3 | 5.9 ± 1.6 | 19 ± 2 | 6 ± 4 |
| 15 | 3.1 ± 0.9 | 14 ± 1 | −0.63 ± 1.1 |

Data are presented as mean ± SEM, n = 6.

The results indicate that the compound of Example 1 dose-dependently inhibits SSAO activity in both rat plasma and liver tissue.

What is claimed is:

1. A process for preparing a compound of Formula 1:

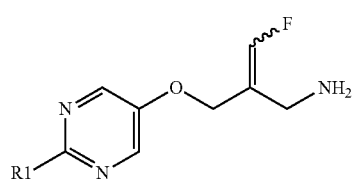

or a pharmaceutically acceptable salt thereof, wherein:
R1 is selected from the group consisting of:

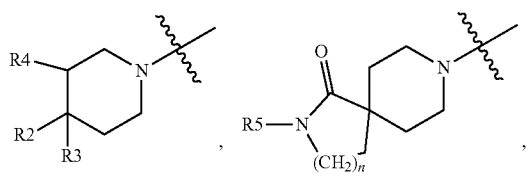

-continued

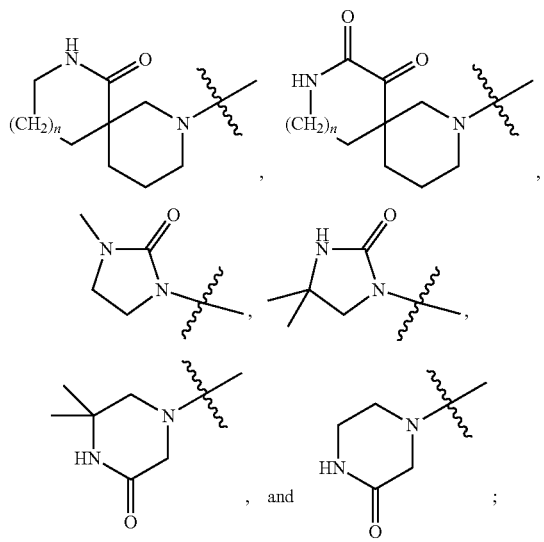

,

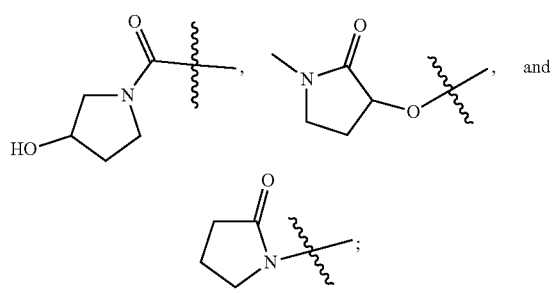

;

R2 is selected from the group consisting of: H, —C(O)NH$_2$, —C(O)NH(CH$_3$), —C(O)N(CH$_3$)$_2$,

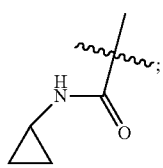 [SMILES: *C(=O)NC1CC1]

R3 is H or CH$_3$;

R4 is H or

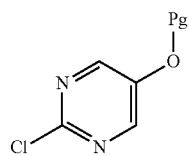

R5 is selected from the group consisting of: H, —C$_{1-4}$ alkyl, —C$_{3-4}$ cycloalkyl, and —CH$_2$—C$_{3-4}$ cycloalkyl; and n is 1 or 2, said method comprising the steps of:

a) reacting a compound of formula A:

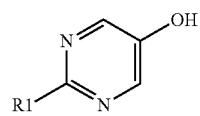

A wherein Pg is a protecting group, with a substituted cyclic amine followed by a deprotecting step to form a compound of formula B:

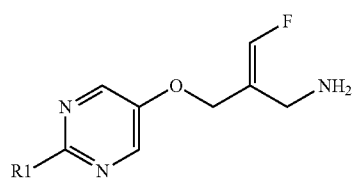

B wherein R1 is as defined for Formula 1;

b) reacting the compound of formula B with a suitable amine-protected 2-bromomethyl-3-fluoro-propyl-2-en-amine, following by a deprotecting step, to form the compound of Formula 1; and c) optionally converting the compound of Formula 1 to a pharmaceutically acceptable salt.

2. The process of claim 1, wherein the compound of Formula 1, or a pharmaceutically acceptable salt thereof, is a compound of Formula 2:

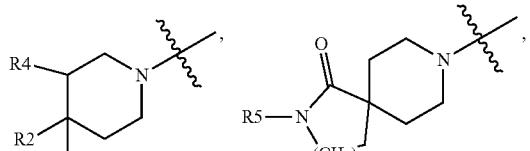

2 or a pharmaceutically acceptable salt thereof.

3. The process of claim 1, wherein R1 is selected from the group consisting of:

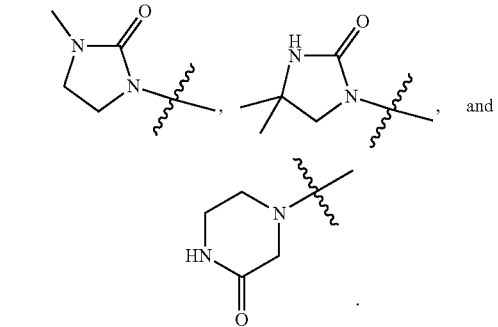

4. The process of claim 3, wherein R1 is:

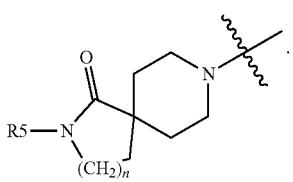

.

5. The process of claim 4, wherein R5 is selected from the group consisting of:

H, —CH₃,

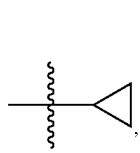

and

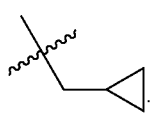

6. The process of claim 1, wherein:
R1 is

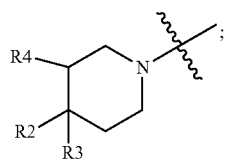

and

R2 is selected from the group consisting of: H, —C(O)NH₂, —C(O)NH(CH₃), —C(O)N(CH₃)₂,

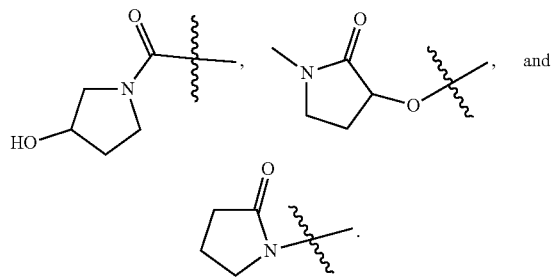

7. The process of claim 6, wherein R3 is H.

8. The process of claim 6, wherein:
R4 is

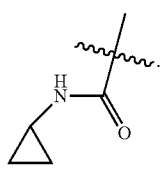

9. The process of claim 1, wherein the compound of Formula 1 is:

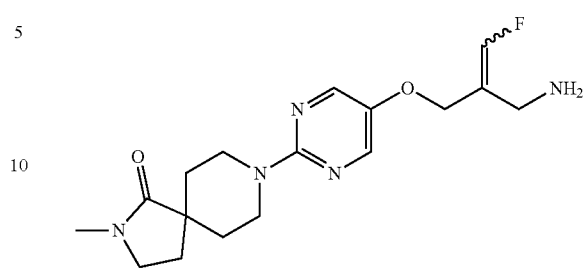

or a pharmaceutically acceptable salt thereof.

10. The process of claim 1, wherein the compound of Formula 1 is:

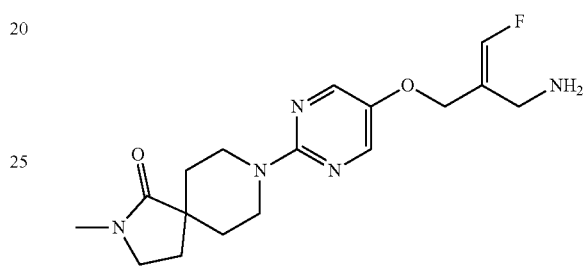

or a pharmaceutically acceptable salt thereof.

11. The process of claim 10, wherein the compound is a mono or a di hydrochloride salt.

12. The process of claim 10, wherein the compound is:

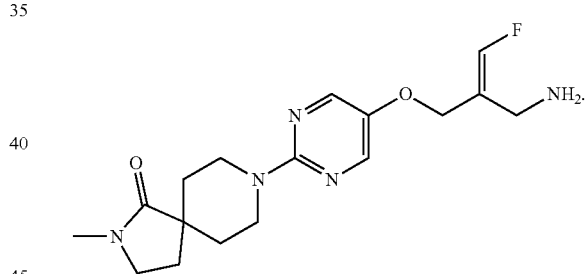

13. The process of claim 1, wherein step a) is carried out in the presence of a base during the reaction of the compound of formula A with the substituted cyclic amine.

14. The process of claim 13, wherein the base is N,N-diisopropylethylamine or potassium carbonate.

15. The process of claim 1, wherein the protecting group of the compound of formula A in step a) is benzyl.

16. The process of claim 15, wherein the deprotecting step of step a) uses palladium-catalyzed hydrogenation.

17. The process of claim 1, wherein the suitable amine-protected 2-bromomethyl-3-fluoro-propyl-2-en-amine of step b) is tert-butyl N-[(E)-2-(bromomethyl)-3-fluoro-allyl] carbamate.

18. The process of claim 17, wherein the deprotecting step of step b) uses an acid.

19. The process of claim 18, wherein the acid is HCl.

* * * * *